(12) United States Patent
Brukilacchio

(10) Patent No.: US 8,278,841 B2
(45) Date of Patent: Oct. 2, 2012

(54) LIGHT EMITTING DIODE LIGHT ENGINE

(75) Inventor: Thomas J. Brukilacchio, Reading, MA (US)

(73) Assignee: Innovations In Optics, Inc., Woburn, MA (US)

(*) Notice: Subject to any disclaimer, the term of this patent is extended or adjusted under 35 U.S.C. 154(b) by 333 days.

(21) Appl. No.: 12/825,611

(22) Filed: Jun. 29, 2010

(65) Prior Publication Data
US 2011/0001431 A1    Jan. 6, 2011

Related U.S. Application Data

(60) Provisional application No. 61/222,499, filed on Jul. 2, 2009.

(51) Int. Cl.
F21V 8/00 (2006.01)
F21V 17/00 (2006.01)
H05B 37/02 (2006.01)

(52) U.S. Cl. ........................... 315/294; 315/152

(58) Field of Classification Search .................. 315/294, 315/152, 155, 291, 149; 362/235, 296.02, 362/249.02, 296.05, 296.07
See application file for complete search history.

(56) References Cited

U.S. PATENT DOCUMENTS

| | | |
|---|---|---|
| 4,915,479 A | 4/1990 | Clarke |
| 5,146,248 A | 9/1992 | Duwaer et al. |
| 6,205,998 B1 | 3/2001 | Winston |
| 6,272,269 B1 | 8/2001 | Naum |
| 6,318,863 B1 * | 11/2001 | Tiao et al. ........................ 353/31 |
| 6,967,986 B2 | 11/2005 | Kowarz et al. |
| 6,968,103 B1 | 11/2005 | Schroll et al. |
| 7,001,084 B2 | 2/2006 | Carpenter et al. |
| 7,234,820 B2 | 6/2007 | Harbers et al. |
| 7,455,410 B2 | 11/2008 | Furusawa et al. |
| 7,481,538 B2 | 1/2009 | Furusawa et al. |
| 2002/0114168 A1 | 8/2002 | Pelka et al. |
| 2004/0022071 A1 | 2/2004 | Cheng et al. |
| 2004/0218390 A1 | 11/2004 | Holman et al. |

(Continued)

FOREIGN PATENT DOCUMENTS

WO PCT/US2010/001867    6/2010

OTHER PUBLICATIONS

Welford, W.T. and Winston, R.,"High Collection Nonimaging Optics", Academic Press, pp. 213-215.

Primary Examiner — Daniel D Chang
(74) Attorney, Agent, or Firm — Francis J. Caufield

(57) ABSTRACT

An LED light engine system that incorporates light emitting diodes (LEDs) with one or more distinct colors, including broad band white light obtained from phosphors or a combination of LED die colors and LED die coated phosphors. The LED die or die arrays are mounted to a high thermal conductivity circuit board comprising COB technology which can include both the LED die and electronic drive components resulting in a compact and reliable design with improved thermal and optical performance. High efficiency non-imaging collection optics are coupled to the LEDs to efficiently capture substantially all of the light which they emit and reformat it as an output with substantially the same éntendue as that of the LED to provide high brightness sources. Feedback from the output back to a photosensor on the circuit board is provided to assure that the output of the collection optic remains constant.

22 Claims, 22 Drawing Sheets

U.S. PATENT DOCUMENTS

| | | |
|---|---|---|
| 2005/0169579 A1 | 8/2005 | Temkin et al. |
| 2005/0224846 A1 | 10/2005 | Imato et al. |
| 2005/0243570 A1 | 11/2005 | Chaves et al. |
| 2005/0275819 A1 | 12/2005 | Tolbert et al. |
| 2006/0043400 A1 | 3/2006 | Erchak et al. |
| 2007/0053200 A1* | 3/2007 | Brukilacchio ............ 362/555 |
| 2007/0206390 A1 | 9/2007 | Brukilacchio et al. |
| 2008/0192477 A1 | 8/2008 | Holder et al. |
| 2008/0205034 A1 | 8/2008 | Kunkel et al. |
| 2009/0073698 A1 | 3/2009 | Tatsuno |
| 2009/0122533 A1 | 5/2009 | Brukilacchio |

* cited by examiner

LIGHT EMITTING DIODE LIGHT ENGINE

CROSS REFERENCE TO RELATED APPLICATION

This application claims the benefit of priority from U.S. Provisional Patent Application No. 61/222,499 entitled LIGHT EMITTING DIODE LIGHT ENGINE which was filed on Jul. 2, 2009 in the name of Thomas J. Brukilacchio, the entire contents of which are incorporated herein by reference.

FIELD OF THE INVENTION

This invention, in general, relates to the collection and monitoring of light emitted from high brightness light emitting diode (LED) die or die arrays coupled into dielectric non-imaging optics and directed toward a monitoring photodiode. Applications cover many markets including commercial, military and industrial illumination where high brightness illumination is required, coupling to optical fibers such as in endoscope, boroscope or microscope illumination, uniform illumination for machine vision, general illumination as in recessed lights, fluorescence imaging, and UV Curing.

BACKGROUND OF THE INVENTION

High brightness light emitting diode (LED) light sources are in high demand for challenging applications to replace conventional light sources that suffer from short life, poor efficiency and often contain toxic elements or compounds. We define an LED light engine as the combination of an LED board with LED die attached and a primary collection optic to, efficiently collect the light and substantially preserve the Etendue (solid angle, area, index squared product) and may include auxiliary electronics including temperature monitoring devices such as thermistors or thermocouples, photosenors for light monitoring, and drive electronics to control the LED drive current and voltage and an electrical connector. Prior art typically utilize tungsten or tungsten halogen, metal halide, and xenon arc lamps for related illumination applications.

Recently, LED based illumination systems have begun to appear in the market, but typically are based on prepackaged LED devices and suffer from relatively poor performance compared to the present invention.

Accordingly, it is a principle object of the present invention to provide a high brightness illumination source utilizing LEDs in combination with non-imaging collection optics.

It is yet another object of the present invention to provide an LED based system in which light is sampled from the output aperture of a collection optic and directed back to an on-board photosensor to allow for continuous monitoring or optical feedback control for applications that need to maintain constant light output or need to know how the light output changes with time and temperature.

Other objects of the invention will in part be obvious and will in part appear hereinafter when the following specification is read in connection with the appended drawings.

SUMMARY OF THE INVENTION

Prepackaged LEDs are defined as devices comprising an LED die or die array sitting on top of one or more thermally and electrically conductive materials each with associated thermal impedance with electrical leads and thermal backplane that are then intended to be attached to yet another board with additional thermal impedance. Examples of prepackaged devices include the Luxeon™ and Rebel™ product lines now sold by Philips, the Osram Dragon™ and Ostar™ product lines, and the CREE X-Lamp™ product line.

The present invention uses "Chip-on-Board" (COB) metal core printed circuit board (PCB) technology in conjunction with high brightness bare LED die attached to the board with solder, eutectic attachment, or conductive epoxy, and high efficiency compact non-imaging optics. This configuration provides a more compact, higher performance, longer life, and lower cost LED light engine relative to systems incorporating pre-packaged LED devices. The thermal impedance between the LED junction and the heat sink is significantly reduced for COB technology by placing the LED die directly on a metal core or on a thin, low thermal impedance dielectric and copper foil layer (or other high thermal conductivity material substrate), thereby increasing temperature dependant life and thermally dependant output power. Additionally, because there is no encapsulant or domed optic over the bare LED die, it is possible to get a much more compact and efficient substantially Etendue (area, solid angle, index squared product) preserving collection optics over the die. Cost is significantly reduced for COB configurations because there is not the additional expense of the components attached to the LED die for the case of pre-packaged LED devices. Additionally, much higher packing densities of LED die are possible, which significantly lowers current density and thereby increases efficiency and lowers total required heat dissipation. In particular for applications requiring a small diameter aperture such as fiber optic illumination, the present invention allows for a much more compact system with higher efficiency relative to one that can be constructed with prepackaged LED devices.

The invention herein is an LED light engine system which incorporates light emitting diodes (LEDs) with one or more distinct colors including broad band white light obtained from phosphors or a combination of LED die colors and LED die coated phosphors. The LED die or die arrays are mounted to a high thermal conductivity circuit board comprising COB technology which can include both the LED die and electronic drive components resulting in a more compact and reliable design with improved thermal and optical performance at lower cost relative to pre-packaged based LED systems and other non LED systems such as the industry standard tungsten halogen lamps, metal halide or Xenon arc lamps. In conjunction with high efficiency non-imaging collection optics, the resulting LED based light engines of the present invention are unmatched in brightness by other commercially available LED based illumination systems.

The light from the typically ultraviolet (UV), blue, green, amber, red, infrared or phosphor coated blue or UV LED die or die arrays is collected by a non-imaging concentrator which is substantially Etendue preserving. Thus, these light engines are ideally suited for applications such as surgical illumination for head lamps or endoscopes which are among the most challenging light applications that exist today.

The combination of COB technology and high efficiency non-imaging optics results in the preferred embodiment of the invention. A particular aspect of the present invention is the method in which light is sampled from the output aperture of the optic and directed back to an on-board photosensor to allow for continuous monitoring or optical feedback control for applications that need to maintain constant light output or need to know how the light output changes with time and temperature. Additionally, there is typically a temperature monitoring device such as a thermistor attached to the board to allow for continuous temperature monitoring and or control.

Another important aspect of a preferred embodiment of the present invention uses a reflective aperture to increase the brightness of the light engine which has particular application to Etendue limited applications such as fiber optic coupling.

BRIEF DESCRIPTION OF THE DRAWINGS

The structure, operation, and methodology of the invention, together with other objects and advantages thereof, may best be understood by reading the following detailed description in connection with the drawings in which each part has an assigned numeral or label that identifies it wherever it appears in the various drawings and wherein.

DETAILED DESCRIPTION

The present invention relates to Light Emitting Diode (LED) illumination systems for which the Etendue (area, solid angle, index squared product) is substantially preserved and has application across many markets including general illumination, fiber optic coupling including microscopes, endoscopes and boroscopes, machine vision and inspection, ultra-violet (UV) curing, medical illumination, projection systems and fluorescence illumination. In particular the present invention offers higher performance in a more readily manufactured and reliable package in comparison to prior art.

An important aspect of the invention is the way the associated collection optic provides a sampling of the light from the LED die, die array or phosphor emitted at the entrance aperture of the optic and passing out the upper portion of the said optic and is then reflected by total internal reflection (TIR) back down the outer wall of the optic toward a photosensor attached to the same LED board. In this way the sampled light is a good representation of the mixed light from the entire entrance aperture and also takes into account any changes in transmission of the optic due to light induced or age related changes in optic absorption.

Figure 1:
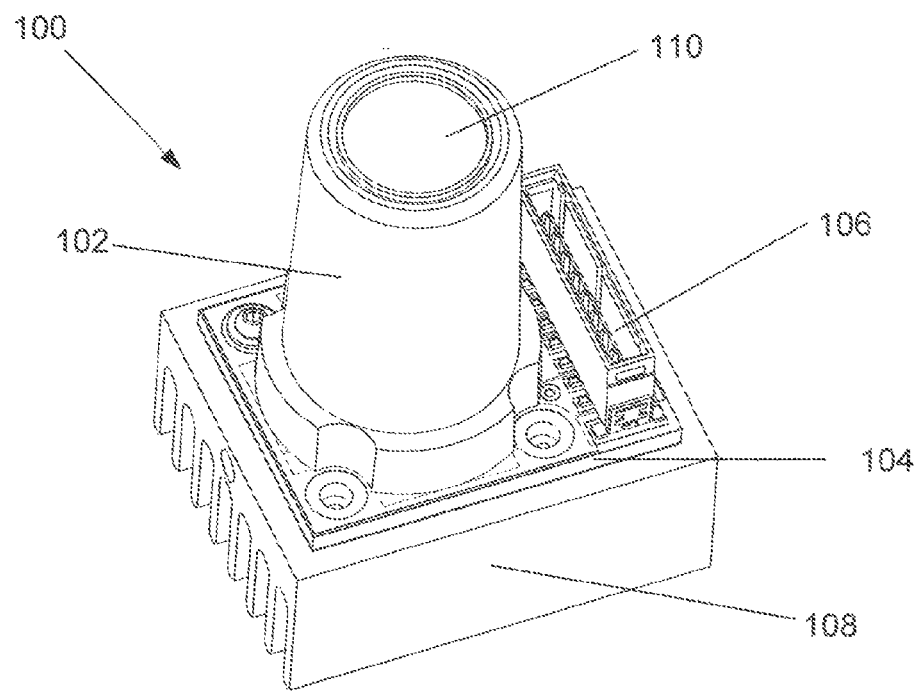
FIG. 1 shows a preferred embodiment of an LED light engine comprisng a heat sink, LED board with LED die and a non-imaging collection optic.

FIG. 1 shows an isometric view 100 of a preferred embodiment of an LED light engine. A high thermal conductivity LED board 104 upon which LED are mounted, as will become apparent shortly, is shown attached to a heat sink 108. A collection optic 102 is attached to the LED board from which light exits at surface 110. A surface mounted multi-pin connector 106 is soldered to the LED board 104. To maintain low LED junction temperature for improved output and lifetime, a high thermal conductivity substrate material such as, but not limited to, copper, aluminum, aluminum nitride, aluminum oxide, beryllium oxide, planar heat pipes, chemical vapor deposited (CVD) diamond, graphite, aluminum and copper composite materials, etc. is used to spread the heat in the plane of the board so as to reduce the heat flux through the back of the board to the heat sink. A thermally conductive material is typically placed between the back of the LED board 104 and the heat sink 108 so as to reduce the temperature rise across that interface. Suitable materials include the silicone/aluminum oxide materials sold under the name Gap Pad or Sil Pad from companies such as The Bergquist Company of Chanhassen, Minn. 55317 USA, standard thermal greases such as those based on aluminum oxide, silver or diamond powders, or Pyrolytic Graphite Sheet (PGS) such as is available from the Panasonic Corporation which is made from a highly oriented graphite polymer film. A multi-pin connector 106 is shown surface mounted to the LED board 104 and is capable of transmitting high currents on the order of 10's of Amps to the LEDs.

Figure 2:
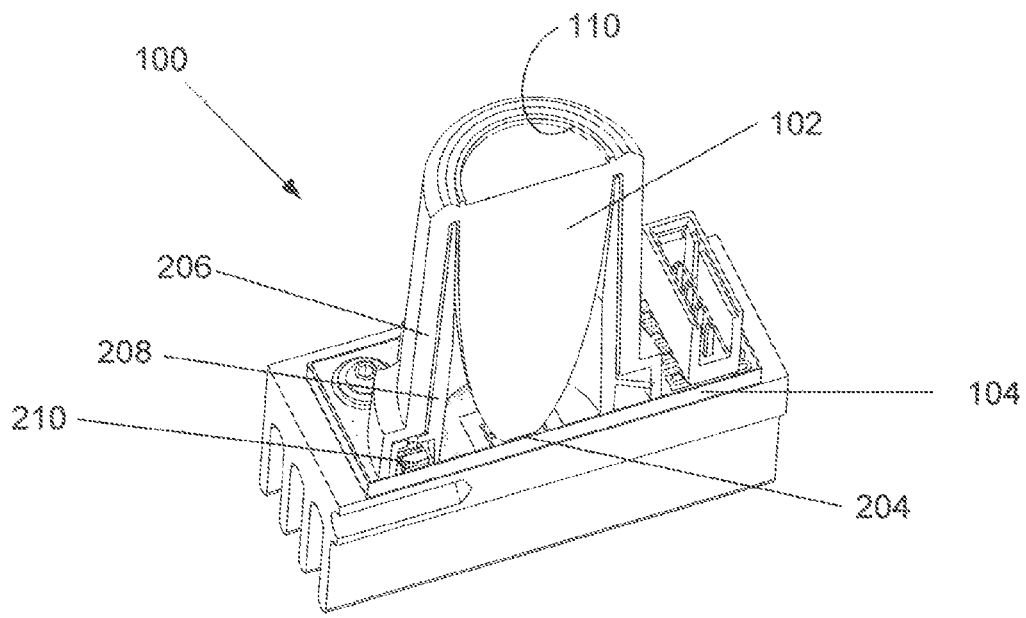
FIG. 2 is a cross sectional view of the system of FIG. 1.

FIG. 2 shows a vertical cross sectional view of the system of FIG. 1 indicating the detail of the non-imaging collection optic 102 having an input aperture 204, a light blocking shroud 208, and a photosensor 210. The LED collection optic 102 is in a preferred embodiment of the form of a compound parabolic concentrator (CPC) such as described by Winston and Welford in a book entitled "High Collection Non-imaging Optics" published by Academic Press and is made of a tilted and shifted parabolic section according to the edge ray principle. Typical dielectric materials used to mold the optic 102 include, but are not limited to, highly transparent optical grade thermal plastics such as acrylic, polycarbonate, cyclic olefins (such as is available from Zeon Chemicals), or other transparent materials such as glass or silicone. A new class of polycarbonate manufactured by Bayer and include products such as LED2045 or LED2245 are particularly well suited due to their resistance to yellowing from exposure to short wavelength blue light or UV wavelengths. Additionally, the Bayer materials have a high glass transition temperature on the order of 147 Centigrade and have robust mechanical properties which yield rugged and reliable devices. The light emitted from the LED die, die array, and/or phosphors attached to the LED board 104, directly under the entrance aperture 204 of the optic 102, first pass through an index of refraction matching gel, typically made out of silicone, such as is available from the Nusil Corporation. The index matching gel increases the extraction efficiency of the light created within the LED die itself due to a reduction of the light totally internally reflected and thus trapped within the LED die. The light reflects off the side walls of the CPC and is directed toward the aperture 110 of FIG. 1 where some of the light around the top outside edge of the optic is directed via a folded optical path by the process of total internal reflection (TIR) back down through an outer wall of the optic 206 toward the photosensor 210. The purpose of the shroud 208 is to block light that would otherwise reach the photosenor by a more direct path. The advantage to sampling the light in this manner is that it represents a good average sampling from all the LED die over the entire input aperture 204 of the optic 102. Additionally, as the optic ages, if it is made out of a polymer material, the increase in the absorption and thus loss of light would affect the light reaching the photosensor 210 and would be a better indicator of the light exiting aperture 110 than if light were to reach the photosensor directly from the LEDs.

Figure 3:
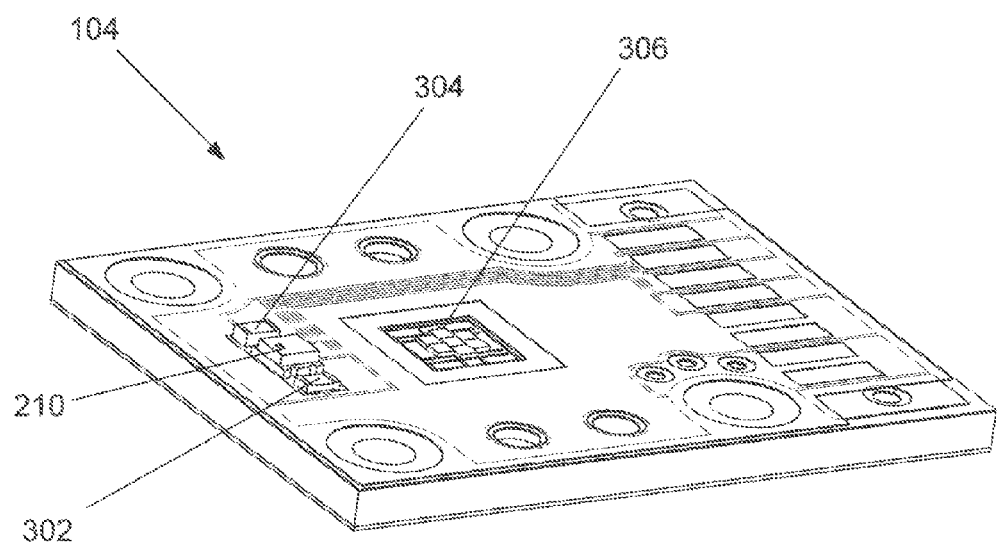
FIG. 3 is a view of the system of FIG. 1 with the heat sink, optic, and connector removed showing LED die, photosensor, thermistor and gain resistor.

FIG. 3 shows a detailed perspective view of the LED board 104 indicating an LED die array 306, photosensor 210 and an associated gain resistor 302, and a thermistor 304.

Figure 4:
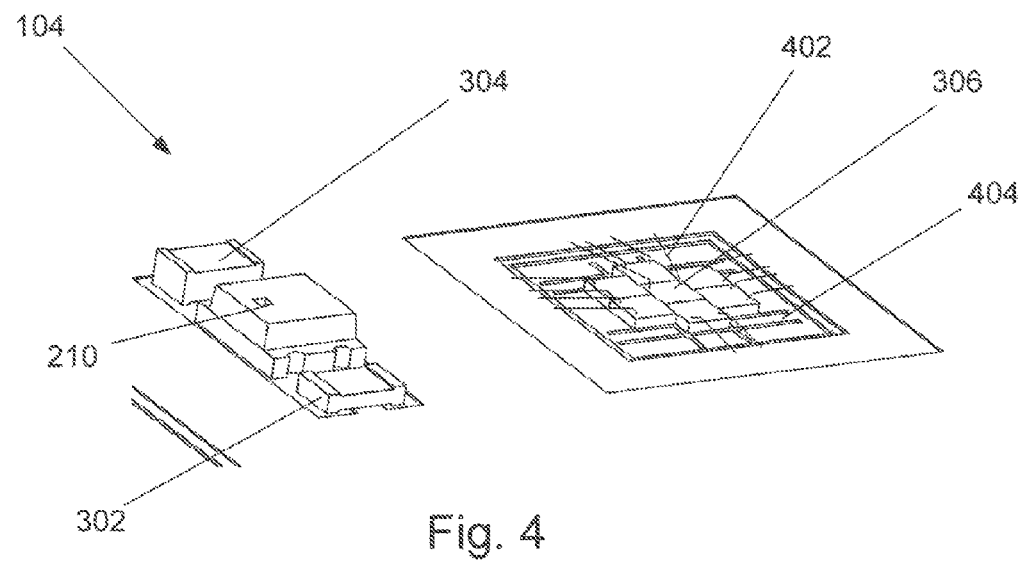
FIG. 4 shows an enlarged view of the system of FIG. 3 indicating the additional detail of wire bonds and alignment scribes for accurate LED die placement.

FIG. 4 shows an enlarged close up view of the semiconductor components on board 104 of FIG. 3. The LED die 306 are attached directly to the gold coated copper substrate using standard attachment materials including solder, direct eutectic attachment and electrically and thermally conductive epoxy to achieve the best thermal performance. Laser scribed lines 404 are shown ablated into the metal substrate to act as alignment references for the die and are themselves aligned to the datums comprising the holes in the board through which kinematic pins in the optic 102 are positioned upon assembly. This assures that the input aperture 204 lines up with the LED die or die array 306. Wire bonds 402 are shown attaching the top side of the LED die to the surrounding contact which is in turn routed to the connector 106.

Figure 5:
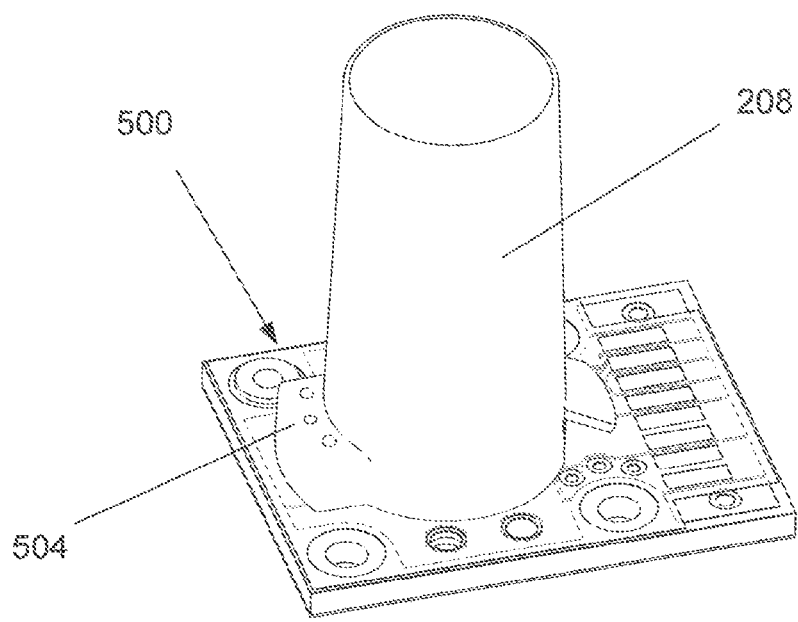
FIG. 5 shows the system of FIG. 3 with the light blocking shroud which was shown in cross section in FIG. 2.
Figure 6:
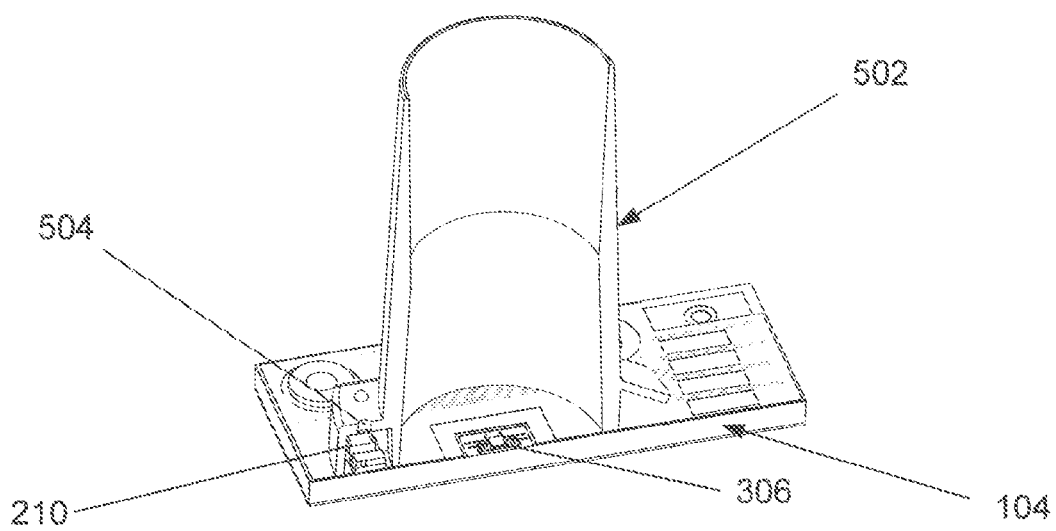
FIG. 6 shows a cross section of the system of FIG. 5.

FIG. 5 shows a perspective view of the LED board 104 with the light blocking shroud 208 attached. The shroud 208 is designed to be held in place by the optic 102. The light enters the shroud 208 at a hole 504 that is centered over the active area of the photosensor 210. A vertical cross sectional view of the system of FIG. 5 is shown in FIG. 6. The portion of the shroud 208 surrounding the photosensor 210 can be seen which acts to block light from the LED die 306 from directly reaching the photosensor.

Figure 7:
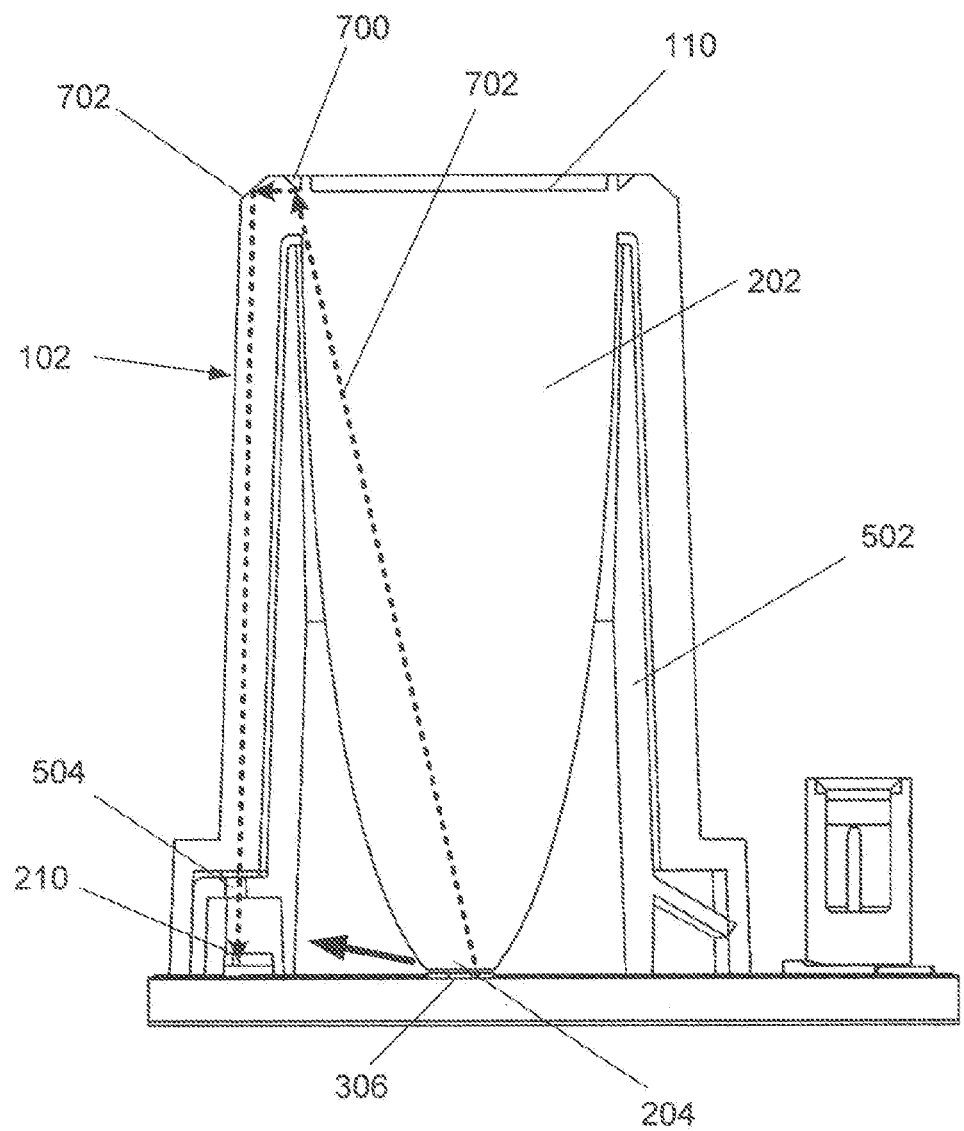
FIG. 7 shows a cross section of the system of FIG. 2 indicating the optical ray paths for the light reflected toward the monitoring photosensor and the blocking of the light by the shroud that would otherwise shunt light to the photosensor.

FIG. 7 shows an enlarged cross sectional view of the system of FIG. 1. A ray path 702 indicated as a dotted line is shown exiting the LED die array 306 through the index matching gel and input aperture 204 toward upper outer prismatic facets, 701 and 702, of the optic 102. Ray path 702 is directed back down toward the photosensor 210 by facets 701 and 702 angled such as to reflect by total internal reflection and pass through shroud hole 504. Since the CPC is molded as a single piece and there has to be some means of attaching the CPC portion to the outer surface of 102, this approach serves double duty by also acting as a light sampling means. The output aperture 110 is recessed to allow the attachment of a thin (0.010 inch) diffuser such as those termed "holographic diffusers" manufactured by such companies as Luminit of Torrance, Calif., or "Engineered Diffusers" by companies such as RPC in Rochester, N.Y. The purpose of the diffuser is to increase the uniformity of the far field intensity distribution or provide an elliptical or rectangular far field by suitable surface structures. Alternatively, the diffusers could also be molded directly onto the output aperture 110 of optic 102. Typically, diffusers are only used for far field applications and are not generally used when coupling the output of aperture 110 to an optical fiber or light pipe or when the near field is reimaged such as in projection applications. The dark arrow emitted from the LED die array 306 indicates that the light is blocked by shroud 502 from reaching photosensor 210 without passing through the CPC 202.

Figure 8:
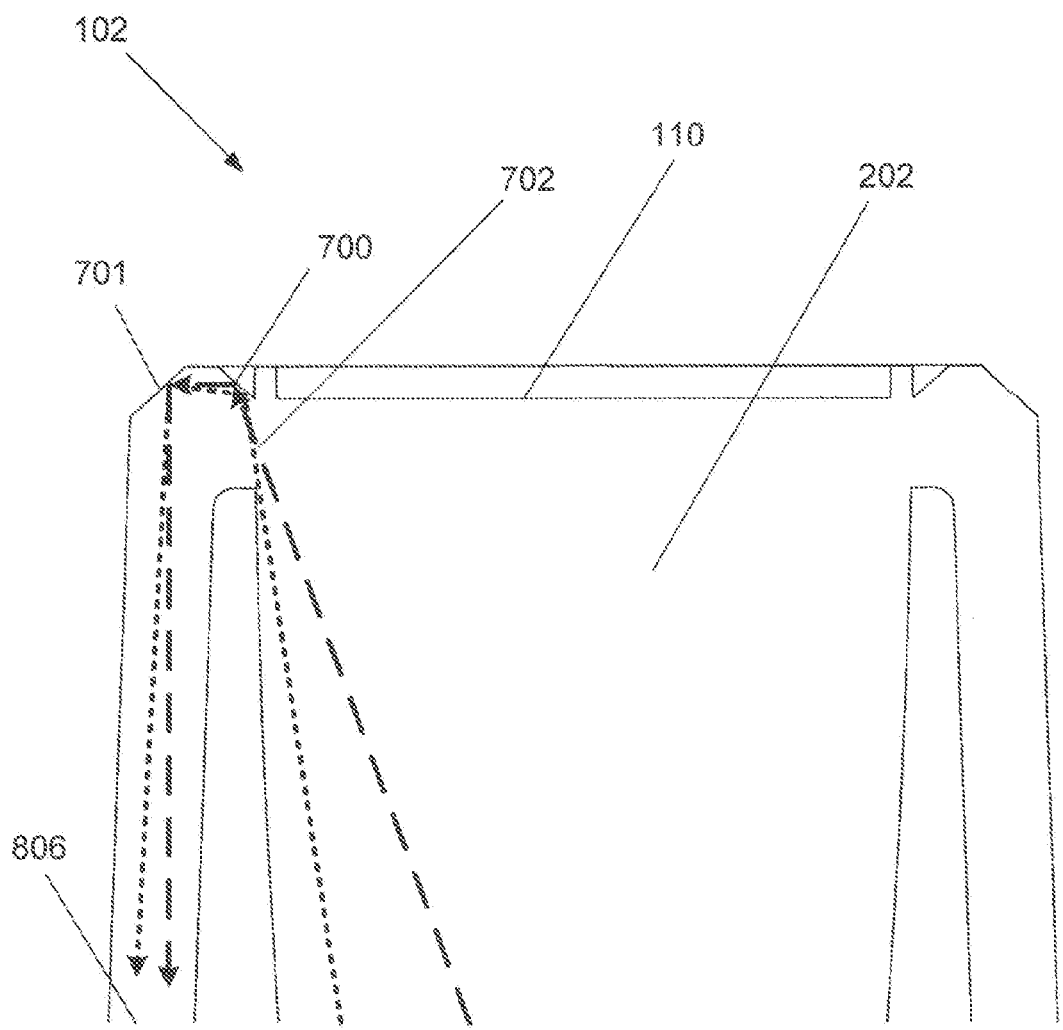
FIG. 8 shows greater detail of the light path for light reflected from the top of the collection optic down toward the photosensor.

FIG. 8 shows an enlarged close up view, with parts broken away, of the optic 102 of FIG. 7 showing two different ray paths 702 reflecting off of facets 701 and 702 down a side wall 806. The efficiency of this geometry was optimized through non-sequential ray tracing using ZEMAX optical design software.

Figure 9:
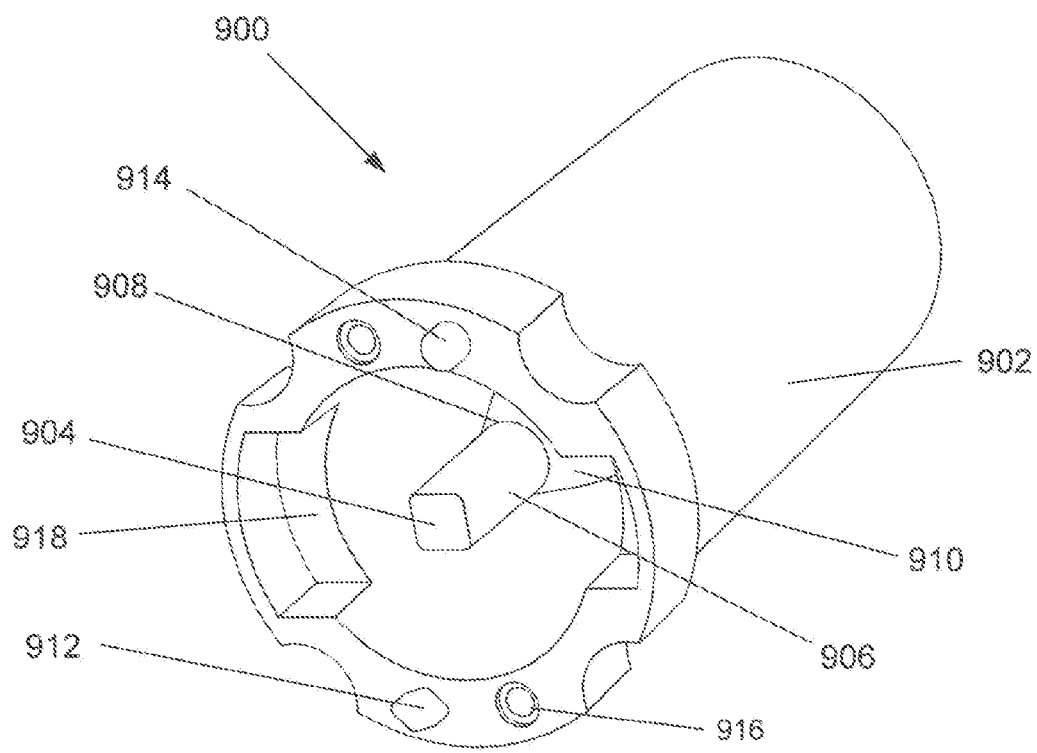
FIG. 9 shows an isometric view of an alternative embodiment of the collection optic of FIG. 1 which comprises a light homogenizing first section coupled into the compound parabolic concentrator (CPC) section.

FIG. 9 shows an alternative embodiment optic 900 of the optic 102 of FIG. 1. Optic 900 was designed to attach to the same LED board 104. Optic 900 was designed specifically for use with no index matching gel. One very important aspect of the invention of FIG. 9 is that there is no index matching gel between the LED die and the input aperture of the collection optic for the purpose of maximizing the effective source intensity by recognizing the role of the index squared portion of the Etendue (index squared, area, solid angle product). Historically, the extraction efficiency of LED die increased by approximately the square of the index of refraction of the index matching gel (about 2 times). However, due to surface extraction enhancement technology used in state of the art LED die, this is no longer generally true. In fact the shorter wavelength GaN LED die (UV through green) only increase on the order of 20% to 40% depending on the LED die manufacturer, and the longer wavelength amber to red and near infrared LED die only increase on the order of 50% to 60% when index matched. Thus, due to the index squared factor of the Etendue, brightness is enhanced by not using index matching gel, which for a fixed Etendue effectively increases the allowed area of the source allowing the LED die to run at lower current densities. Additionally, in the case of broad band white LED light, which is typically derived by coating blue LED die with a phosphor and silicone mixture, the LED is already index matched, and there is minimal increased output from using index matching gel. The phosphor would be of a type such as cerium doped YAG (Ce:YAG) that is well-known in the art or one of the alternative yellow phosphors available from companies such as Internatix of Fremont, Calif. A portion of the blue light emitted by the LED die would be absorbed by the phosphor and re-emitted as yellow light which, in combination with the scattered but non-absorbed blue light, produces the appearance of white light. Typically, the phosphor is held in place on the emitting surface of the LED die with a silicone material. In a preferred embodiment, the phosphor would be applied by a method shown in pending International Patent Application (WO 2007/064342) which describes a conformal coating process to achieve optimal color uniformity and intensity. Many pre-packaged LEDs are encapsulated, which means they will result in effectively lower brightness relative to non-index matched LEDs on COB.

Figure 10:
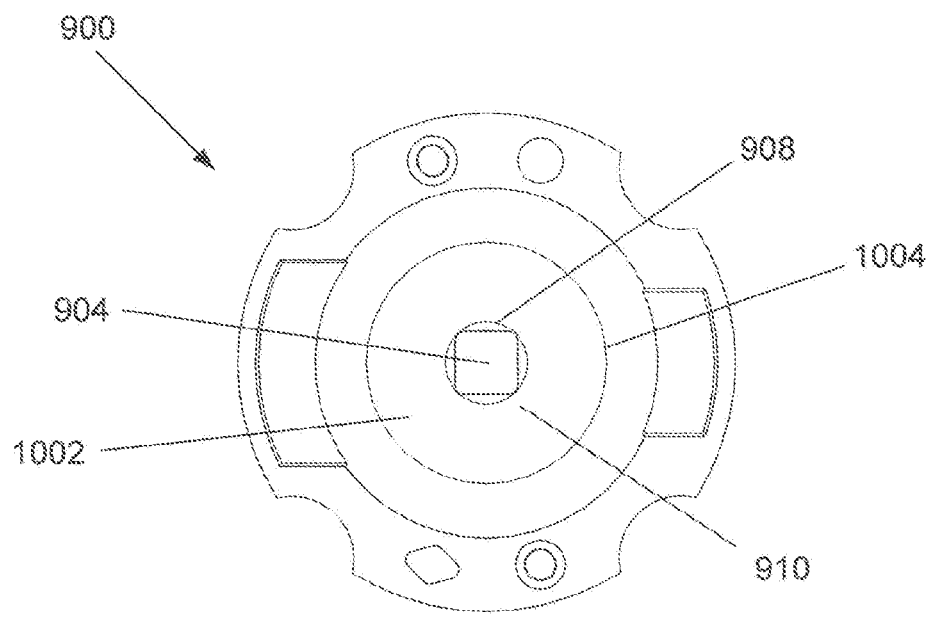
FIG. 10 shows a bottom view of the optic of FIG. 9.

Light from the LED die or die array or die and phosphor would enter the optic 902 at an input aperture 904. The input aperture 904 is square to optimally match the shape of the LED die or die array, which is also square. A section 906 in this example has a length on the order of 10 mm and transitions from the square cross section of input aperture 904 to the circular cross section at the CPC entrance aperture 908. Since this is effectively a non-index matched CPC, the first section of the CPC 910 is conical as the light just inside the CPC has an angle less than 90 degrees dictated by Snell's Law ($n_1 \sin \theta_1 = n_2 \sin \theta_2$). Thus, the collection optic becomes a $\theta_{on}$ by $\theta_{out}$ concentrator also described by Winston and Welford for which a finite input angle is converted to a smaller finite output angle. The features on the bottom of optic 902 are similar to those of optic 102 of FIG. 1. A kinematic pin 914 interfaces to a tightly toleranced hole on LED board 104. A pin 912 on optic 902 fits into another hole on LED board 104 locking the optic in the rotation axis. The tangential dimension of pin 912 is greater than its radial dimension to prevent any issues with fit due to manufacturing tolerance in the distance between the holes on the board versus the distance between the pins on the optic. Holes 916 on opposite sides of the bottom of optic 902 are for self tapping plastic screws which lock the LED board 104 to the optic 102. An indented area 918 on the bottom of optic 902 provides room for the shroud 502 (See FIG. 6) in the vicinity of the photosensor hole 504. The surface of 918 is smooth to allow for the light sampled from the output aperture 110 to be directed with minimal scattering toward the photosensor. FIG. 10 shows a bottom view of FIG. 9. The conical section 910 leads into the CPC section 1002 and joins the top of the optic in a circular cross section at 1004.

Figure 11:
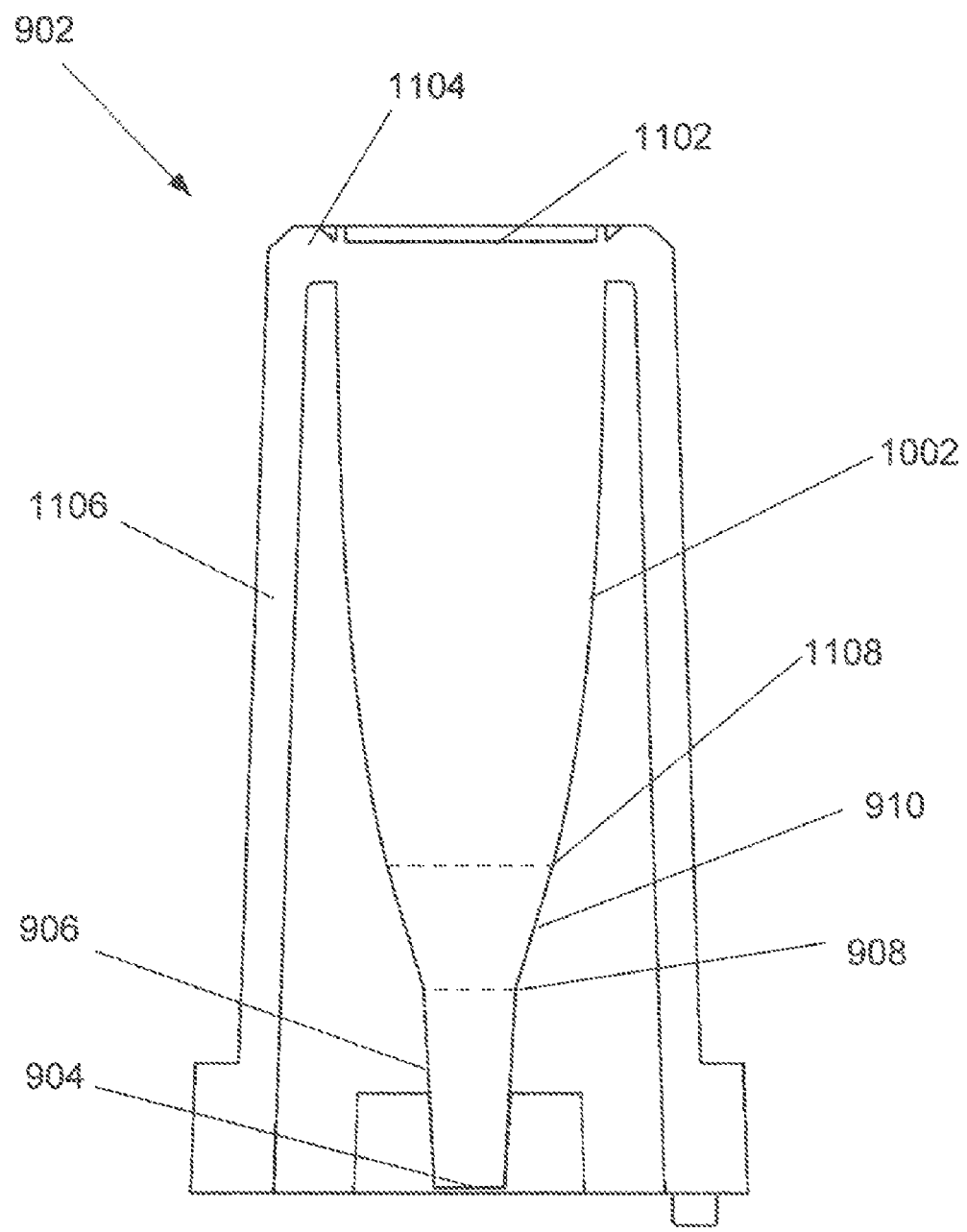
FIG. 11 shows a cross sectional view of the optic of FIG. 9.

FIG. 11 shows a cross sectional view of optic 902. Light enters the optic at 904 from the LED die, die array, phosphor or both die and phosphor combination and is homogenized in the near field as it passes down light integrating section 906 toward an entrance 908 of the collection optic $\theta_{in}$ by $\theta_{out}$ CPC. It is important to note that a CPC is highly efficient at preserving the Etendue and thereby maintains the smallest output aperture for a given maximum extent output angle providing the highest brightness. In fact about 96% of the light that enters the CPC is emitted within the solid angle defined by Etendue matching. While the output of the CPC is very uniform both in the near and far fields for a uniformly filled input, both the near and far field can show structure if the input is not uniform. Thus, the light homogenizing effect of the light integrator section 906 results in a much reduced dependence of output near and far field uniformity on the input near field uniformity. Typically, both the output from LED die and phosphors are substantially Lambertian sources (fall off as the cosine of the input angle) so the only consideration is for near field uniformity not far field uniformity at the input of the CPC section 908. By virtue of the draft angle between apertures 904 and 908, the light entering aperture 908 is slightly reduced in far field angle from that just inside aperture 904 which is taken into account by opening up the input aperture of the CPC. Shaping the input aperture 904 to match the square shape of the LED die array maximizes brightness and maintains the Etendue of the LED or phosphor sources. The homogenizing effect of section 906 also allows multiple colored LED die, or the combination of LED die and phosphors, to be used with excellent near and far field uniformity at an exit aperture 1102. For example, blue LED die and red LED die can be used at the input aperture 904 to achieve both high Color Rendering Index (CRI) and a controlled Correlated Color Temperature (CCT) simultaneously. The manufacturing process can be simplified by coating both the blue die and red die with phosphor, as the red die wavelengths are not absorbed by typical phosphors and the index matching effect of the phosphor/silicone combination used to coat the LED die compensates for losses due to back scattering. Likewise, multiple LED die colors such as red, green and blue can be used in combination to give precise control over the output spectrum without suffering from uniformity issues in the near or far fields due to the sensitivity that would otherwise exist for non-uniform input intensity distributions. The dotted line at 1108 indicates the transition between the conical section 910 of the $\theta_{in}$ by $\theta_{out}$ CPC and the parabolic section 1002. Again the output aperture 1102 is designed to accommodate a diffuser to change the output far field if desired for specific applications.

Figure 12:
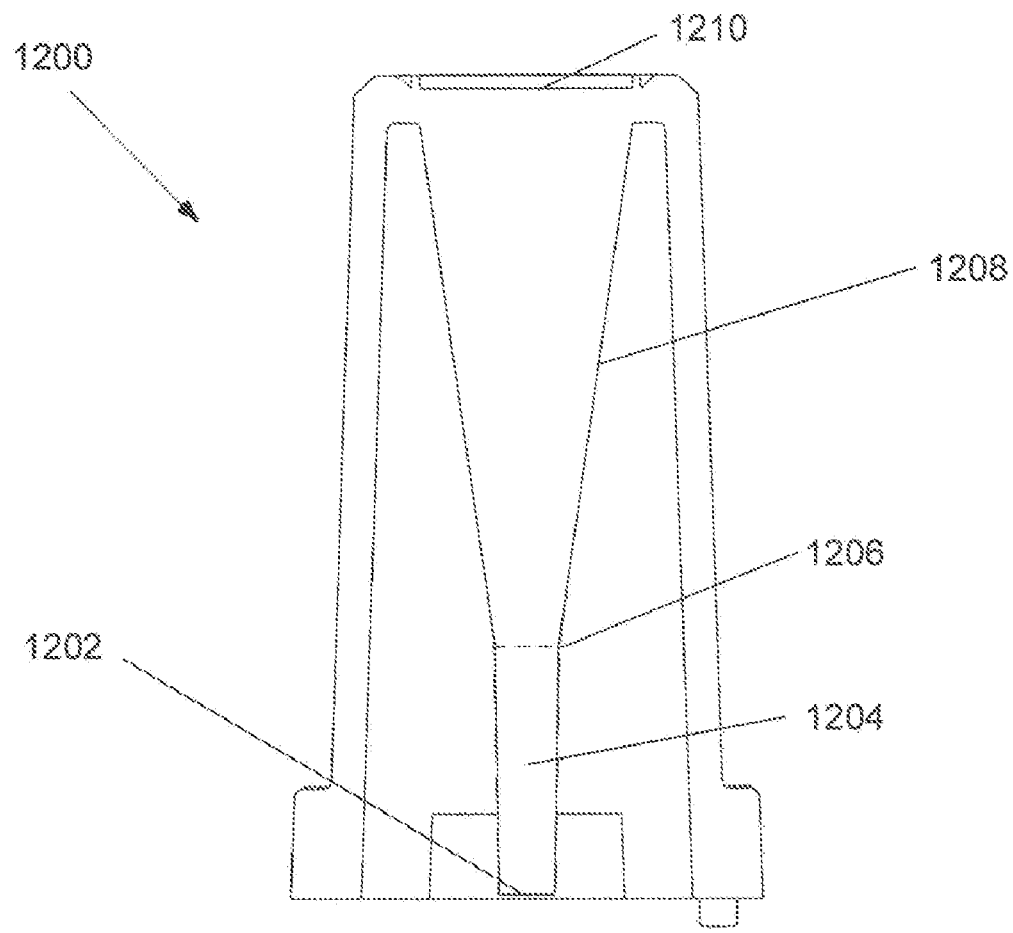
FIG. 12 shows an alternative embodiment of the optic of FIG. 1.
Figure 13:
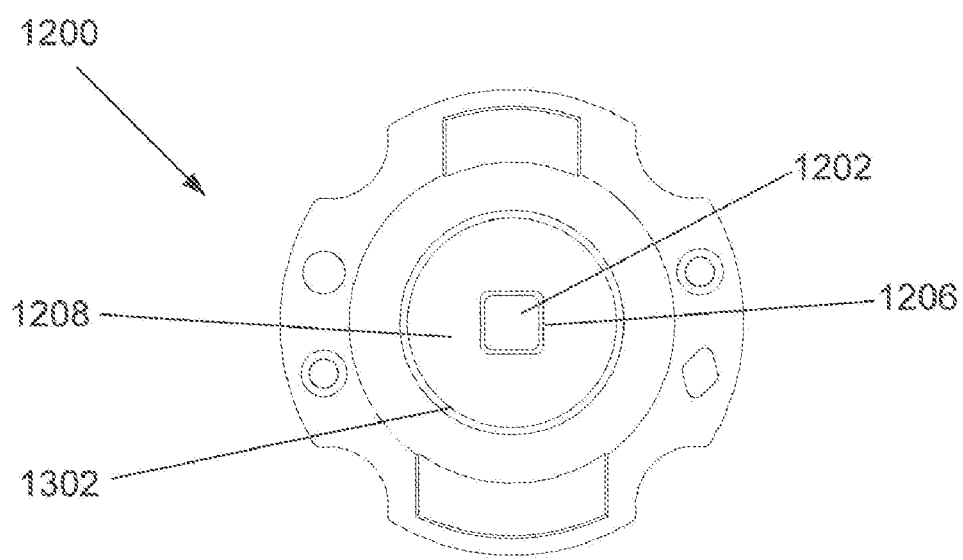
FIG. 13 shows a bottom view of the optic of FIG. 12.

FIGS. 12 and 13 show an alternative embodiment 1200 in cross section and in bottom view, respectively, to the optic of FIG. 9. In this case, the input and output apertures, 1202 and 1206, of a homogenizing section 1204 are both square in cross section. Other shapes can also be used as homogenizers including rectangles, and polygons with an even number of sides. Typically, polygons with an odd number of sides are not as effective at homogenizing, and round cross sections only homogenize in the tangential, not the radial directions, but could be used as well; however, not as effectively. The unique optic section 1208 is formed by lofting the square cross section of 1206 with the round cross section of aperture 1302 such as can be done using SOLIDWORKS computer aided design software.

Figure 14:
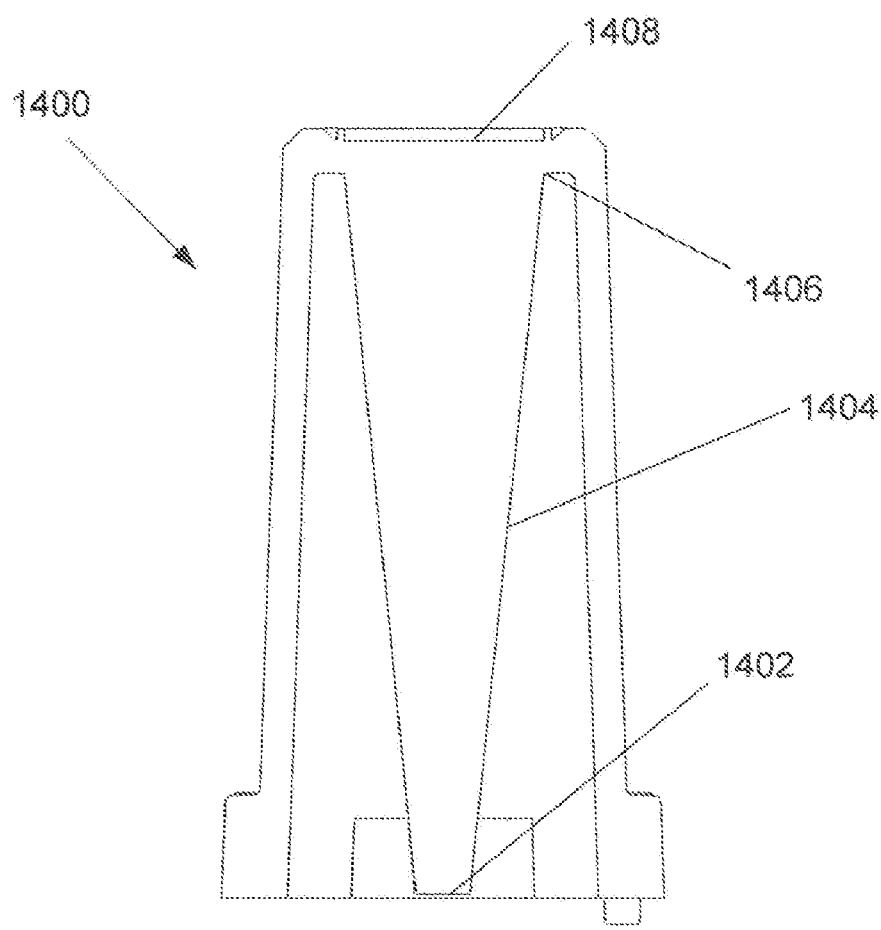
FIG. 14 shows an alternative embodiment of the optic of FIG. 1.
Figure 15:
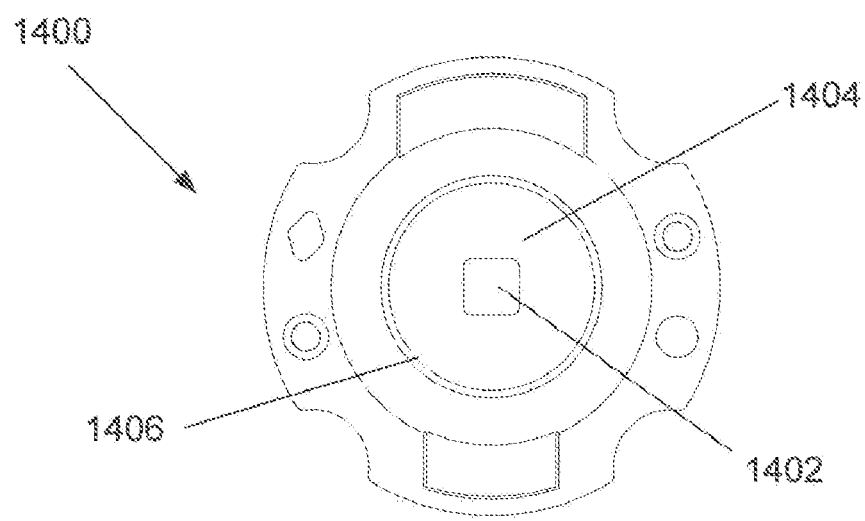
FIG. 15 shows a bottom view of the optic of FIG. 14.

FIGS. 14 and 15 represent another alternative embodiment to the collection optic of FIG. 9 It is designated at 1400 and is shown in cross sectional view in FIG. 14 and in bottom view in FIG. 15, respectively. An optic 1404 is square at an input 1402 and circular at 1406 and is therefore similar to the section 1208 of FIG. 12, but runs the full length of the optic and does not contain a light integrating section.

Figure 16:
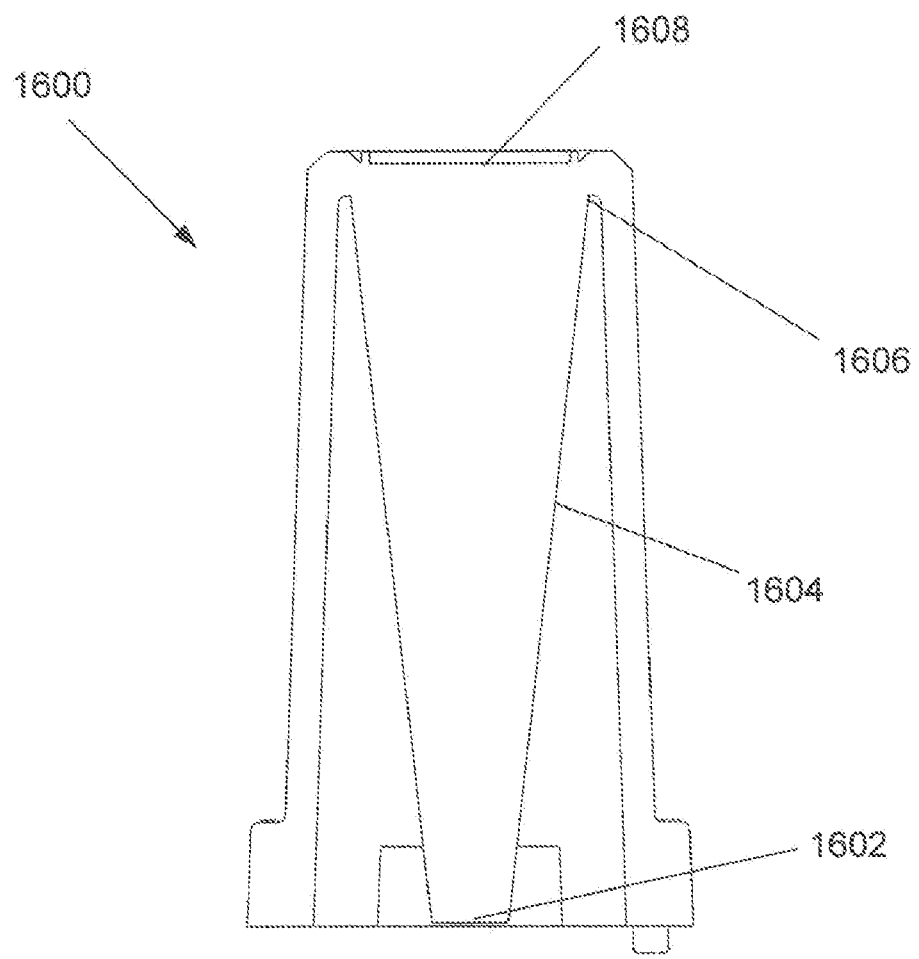
FIG. 16 shows another embodiment of the optic of FIG. 1 comprised of a square cross section taper.
Figure 17:
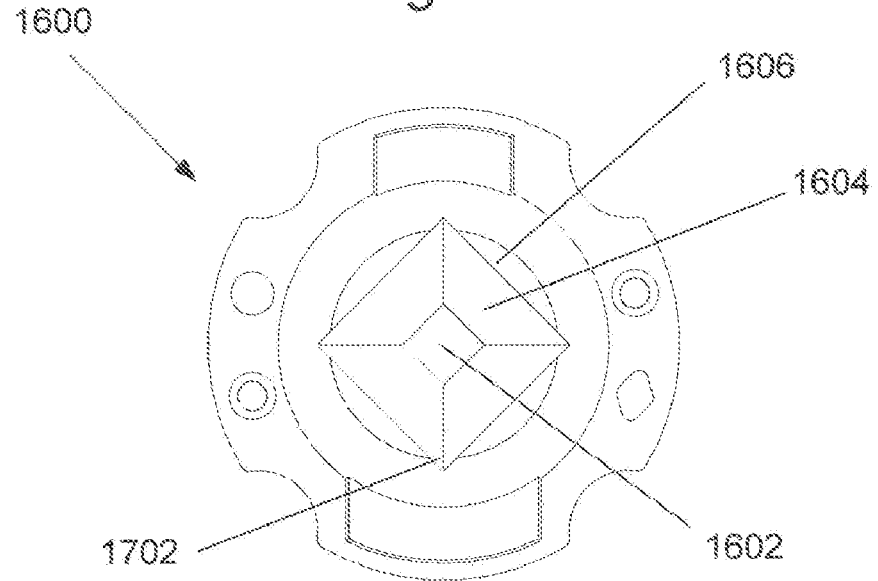
FIG. 17 shows a bottom view of the optic of FIG. 16.

FIGS. 16 and 17 show cross sectional and bottom views 1700 of another alternate embodiment to the optic of FIG. 9, designated at 1600 and also intended for use without index matching gel. Light enters a square cross section input aperture 1602 positioned over a similarly shaped LED die, die array, phosphor coated die or die array or combination thereof. The light is guided by total internal reflection up the square cross section optic 1604 to the output at square cross section 1606 and then through output aperture 1608. The far fields of both the round and square tapered collection optics of FIGS. 9 through 17 are substantially circular. Alternatively, the sides 1604 of the optic of FIGS. 16 and 17 could be similar in profile to the sections 910 and 1002 of FIG. 11 and would in fact have a similar cross section. In this case, however, the far field is substantially square. In fact the far field's aspect ratio would be controlled by the aspect ratio of the output in an inverse relationship according to the brightness theorem for which the product of the face dimension along a particular axis and the numerical aperture (NA which is sin(θ) of the output angle). Thus, the long dimension of a rectangular output produces the narrow dimension of the rectangular far field and the shorter dimension produces the wider far field. Note that the corner of the output aperture of the optic of FIG. 17 overlaps the facets in the vicinity of 1702 to allow for light to be sampled back to the photosensor in the same manner as described for the optic of FIGS. 1 and 9. Thus, the LED array is rotated by 45 degrees along the optical axis to achieve this condition.

Figure 18:
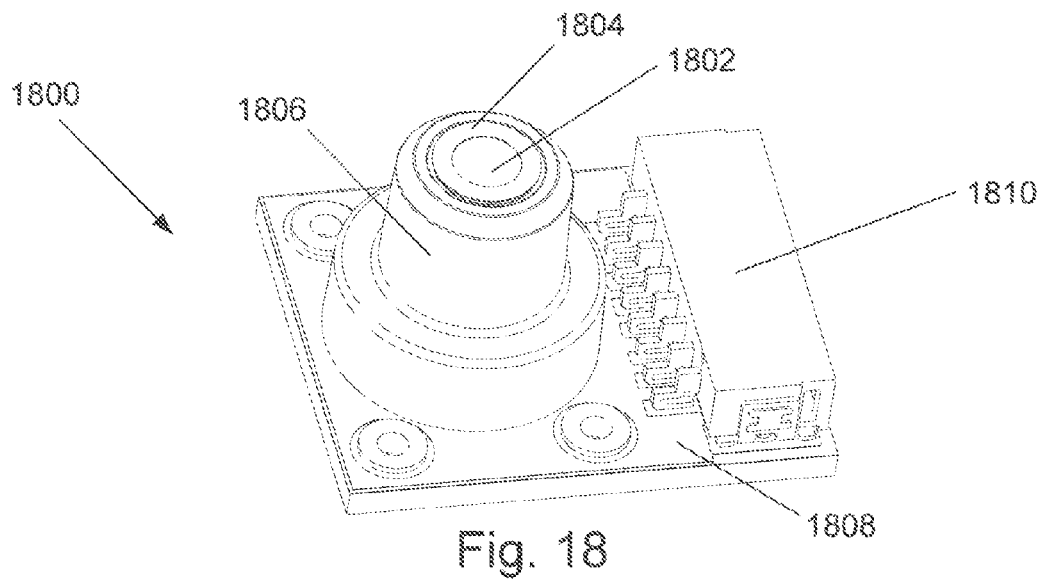
FIG. 18 shows another embodiment of the system of FIG. 1 with a mirrored aperture positioned at the output face of the collection optic for the purpose of increasing the brightness out of the central aperture.
Figure 19:
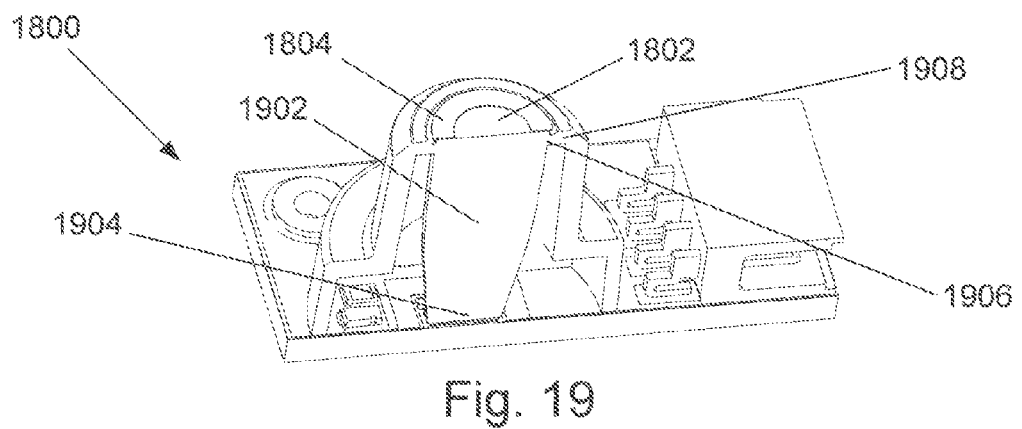
FIG. 19 shows a cross section of the system of FIG. 18.
Figure 20:
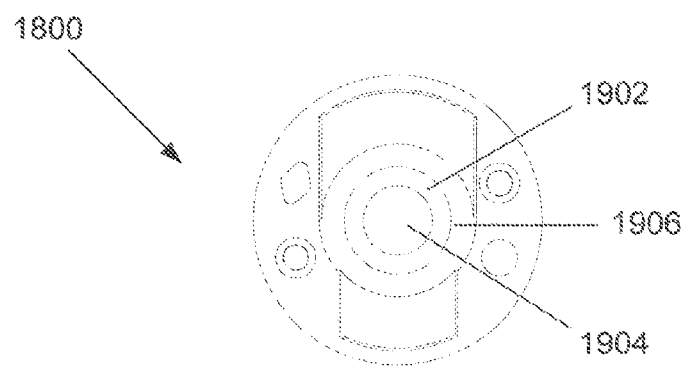
FIG. 20 shows a bottom view of the optic shown in the system of FIG. 18.

FIGS. 18 through 22 show an alternative embodiment to the LED light engine of FIG. 1. The alternative embodiment is designated at 1800 shown in isometric view in FIG. 18, cross sectional view in FIG. 19, bottom view in FIG. 20, isometric cross sectional view in FIG. 21, and enlarged cross sectional view in FIG. 22, respectively. An output aperture 1802 of an optic 1806 in FIG. 18 shows a mirror 1804 with reflective side toward the optic centered on output aperture 1802. An LED board 1808 and connector 1810 are similar to board 104 and connector 106 of FIG. 1. With reference to cross section of FIG. 19, light enters this non-index matched CPC at input aperture 1904 and is directed toward the output aperture 1802 and mirror 1804 either directly or by total internal reflection off the sides of optic 1902. FIG. 20 shows the circular cross section of optic 1902 at both the input aperture 1904 and output aperture 1906. The ray path of a ray 2108 is shown in isometric cross sectional view of optic 1806 in FIG. 21 indicating how it first enters aperture 1904 then passes up toward mirror 1804 which reflects it back toward the input aperture 1904 to the LED array shown just below aperture 1904 where it is subsequently scattered back through the output aperture 1802. In this way, the brightness of the output aperture 1802 within the central aperture of mirror 1804 is increased from what it would otherwise be in the absence of mirror 1804. This enhancement of brightness is useful in Etendue limited applications requiring very high brightness, such as endoscopic fiber bundle illumination which is typically accomplished by use of a high intensity discharge short arc Xenon or Metal Halide lamp. Due to the finite losses at reflecting or scattering interfaces, this approach necessarily reduces efficiency, but does yield higher brightness (power per unit angle per unit area) than other approaches. Typically, increases in brightness on the order of a factor of 2 can be realized by this method, but there are diminishing returns as the ratio of the optic aperture to the mirror aperture increases. Typical reflectivity for state of the art LED die is on the order of 80% for UV through green wavelengths and the order of 60% or better for amber through near infrared (NIR). Phosphors such as Ce:YAG and others made specifically for LEDs typically have quantum efficiencies near unity, so they work extremely well in reflection. The light reflected in the blue spectrum thus has a chance to get partially reabsorbed and emitted as yellow light with most of the non-absorbed light being reflected back toward the output aperture. In this way, there is a yellow shift (toward lower CCT) between the bare phosphor coated LED and the output with the optic with mirrored aperture. Thus, the thickness of the phosphor coating on the LED is reduced from what it would be in the absence of this light feedback for a given CCT specification and thereby reducing the light scattered back toward the LED die as it originally exits the die. This can offset some of the efficiency loss do to the reflective and scattering efficiency described previously. If more than one color of LED die or the combination of LED die and phosphors with different colored LED die are used there is the additional benefit of this approach in that it tends to increase the mixing or homogenization of the light in the near field. The mirror 1804 could be made out of a number of materials. For example, 3M markets a reflective sheet under the product name Vikuiti™ Reflective Display Film with reflectivity on the order of 98%. The film can be attached by adhesive or by other optically transparent cements, epoxies or adhesives.

Figure 22:
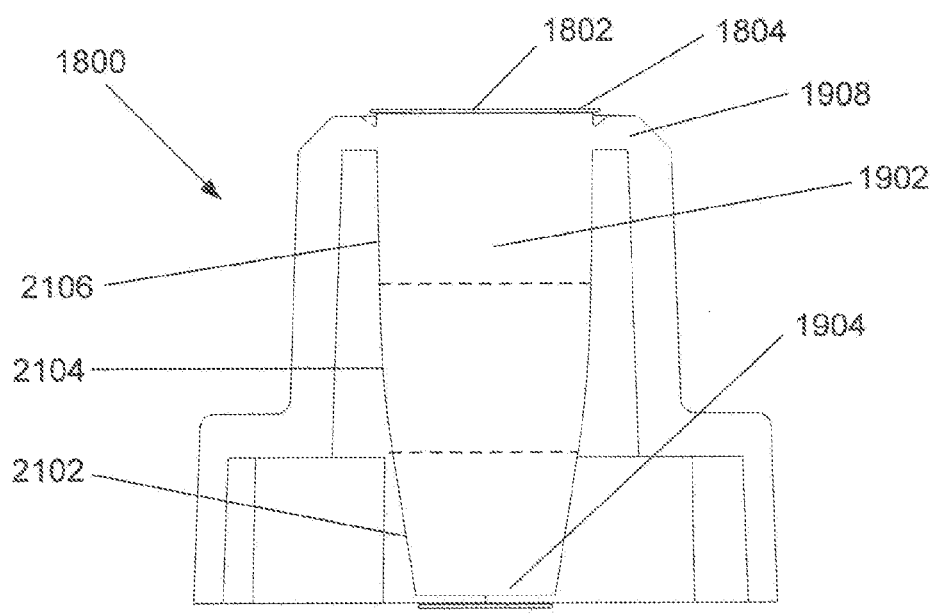
FIG. 22 shows a side view of the optical section of FIG. 21.

The shape of the optic 1902 in the cross-sectional view of FIG. 22 is analogous to that of the optic of FIG. 11 in that the optic 1902 is designed to work without index matching gel and is, therefore, comprised of the conical input section 2102, which is tangent to the CPC parabolic shape 2104 at the interface between them as indicated by the dotted line. The section 2106 is also conical and tangent to the section 2104 at the dotted line between these two sections and is done for the purpose of maintaining sufficient draft angle toward the top of the optic to make it easier for the optic to be released from the mold. The basic design approach for this type of optic is to design the input aperture as if it were to be index matched and thus a standard CPC with no conical section, taking proper account of the index of refraction of the dielectric medium and the surrounding medium which is typically air. One then opens the input aperture up to what it would be for a similar exiting Etendue (diameter and angle) and requires the conical section to be tangent to the parabolic section of the CPC, thus determining the angle and length of the conical section 2102. The slight draft of section 2106 has only a minor effect on the output diameter and angle, but can be accounted for in design optimization by the use of non-sequential design software such as TRACEPRO, ZEMAX, FRED, ASAP, and LIGHT TOOLS. Alternatively the input and output apertures of this optic could both be square or rectangular in cross section to match the shape of the die for smaller apertures. Note, however, that in the case of using phosphor, the area surrounding the LED die would be diffusely reflective assuming it was coated with phosphor.

Figure 21:
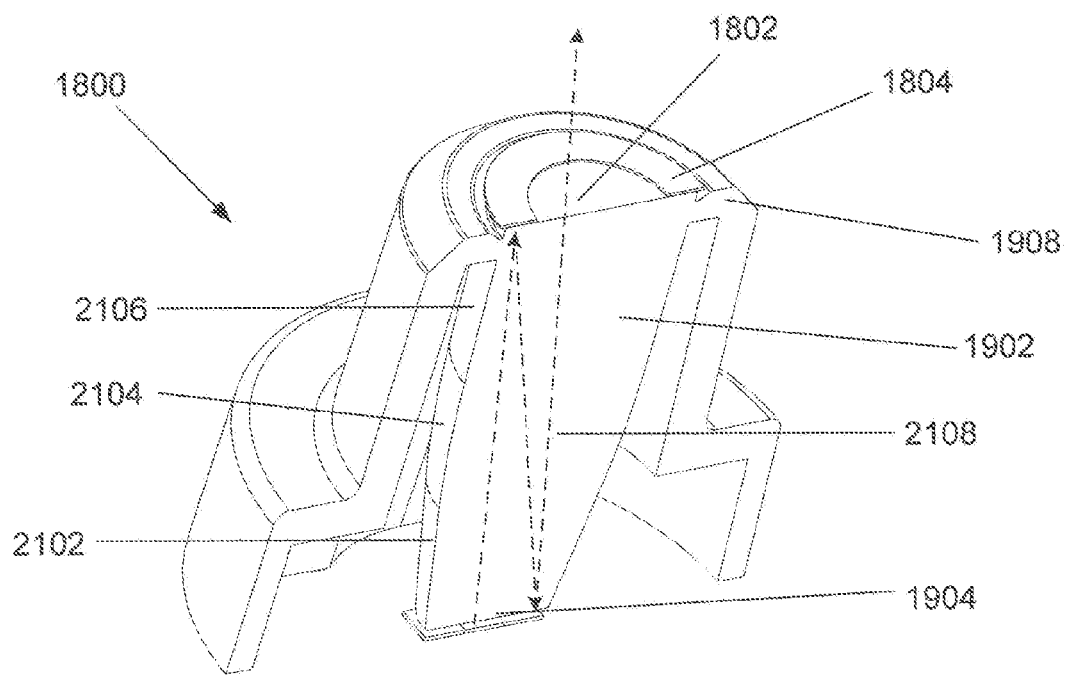
FIG. 21 shows a more detailed view of the optic of FIG. 19 indicating the path of a ray reflected off the mirrored aperture which is scattered off the LED and back out the output aperture.
Figure 23:
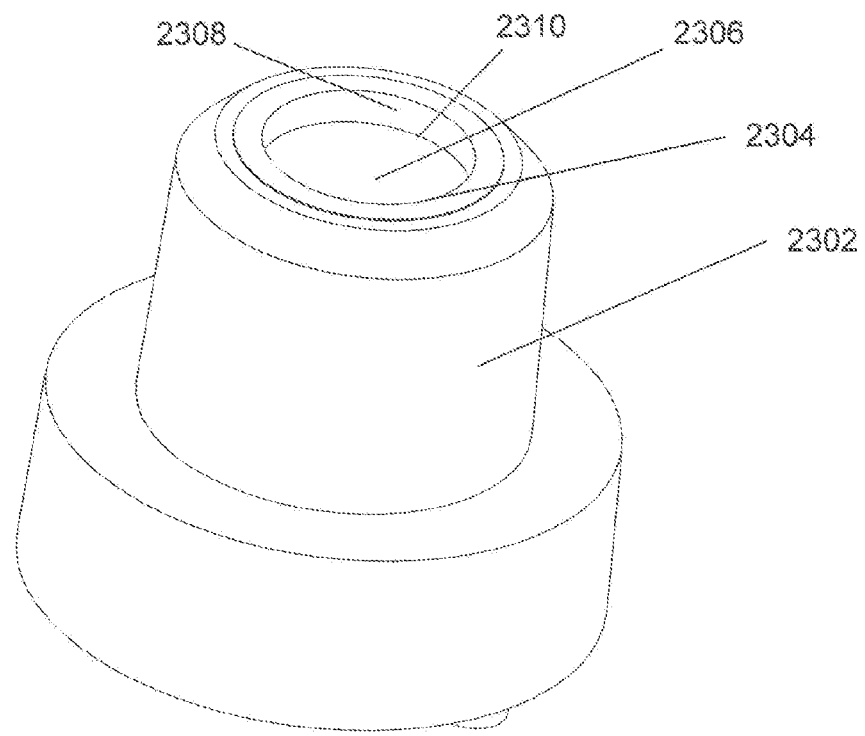
FIG. 23 shows another embodiment of a collection optic and optic holder.
Figure 24:
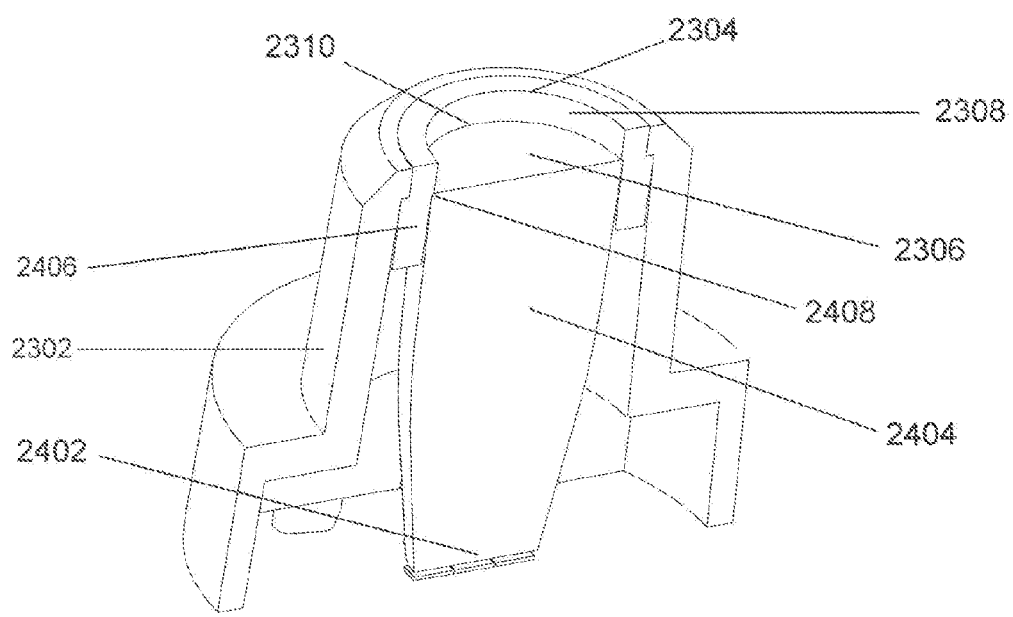
FIG. 24 shows a cross sectional view of the system of FIG. 23.

FIGS. 23 through 28 show an alternative embodiment to the optical configuration of the optic of FIG. 18. FIGS. 23 and 24 show an isometric view of an optic holder 2302, a collection optic 2404 with output aperture 2306, and a reflective interface component 2406 with aperture 2310, side reflective wall 2308 and top aperture 2304. FIG. 24 shows greater detail of the system of FIG. 23 in cross sectional view. The optic 2404, which could have a shape analogous to that of optic 1902 of FIG. 21, is held into interface component or optic holder 2406 which, in turn, is held into surrounding holder 2302. The inside lip 2408, which interfaces to optic output face 2306, can be reflective so that any light incident on it has an opportunity to be reflected back to the LED array below input aperture 2402 and be subsequently scattered back through optic 2404 and out through apertures 2310 and 2304. This type of method for holding the optic is particularly useful for glass versions of the optic which would be used for high power density short wavelength optics that would otherwise be negatively affected by aging affects due to yellowing if they were made of polymers or melting due to high temperature operation. While it is feasible to mold the entire component out of glass, it is not very easily manufactured. The optic holder 2302 would optimally be made out of a high temperature material with an expansion coefficient closely matching that of the optic so that the distance between the input aperture and the LED die array did not change significantly with changes in temperature. Otherwise, the optic could potentially be damaged at extreme temperatures or the wire bonds could be compromised.

Figure 25:
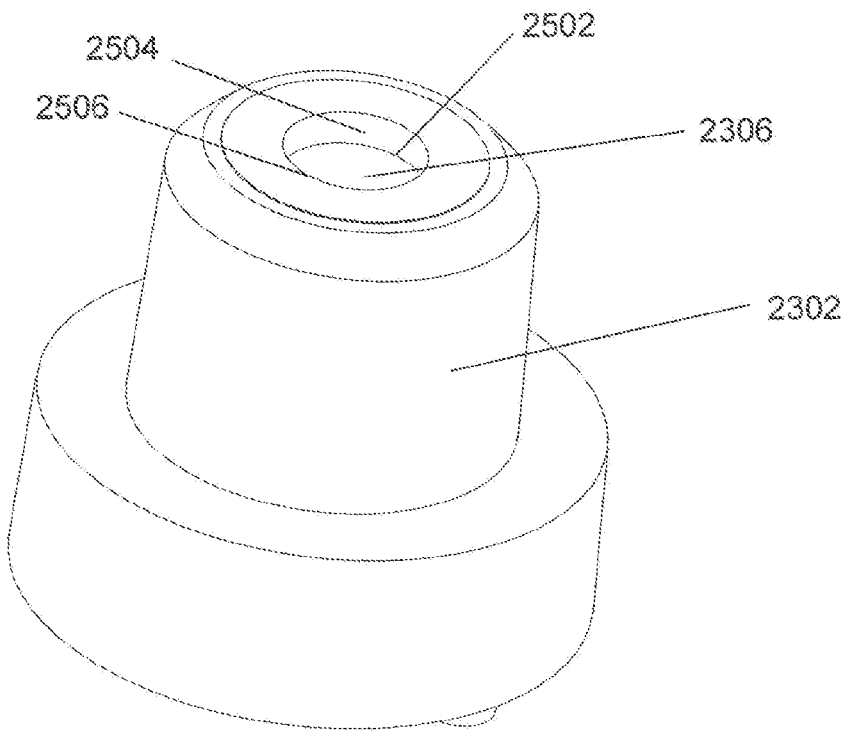
FIG. 25 shows a second embodiment of the system of FIG. 23 with a reduced mirrored aperture holder to increase brigthness of the output analogous to the system of FIG. 18.
Figure 26:
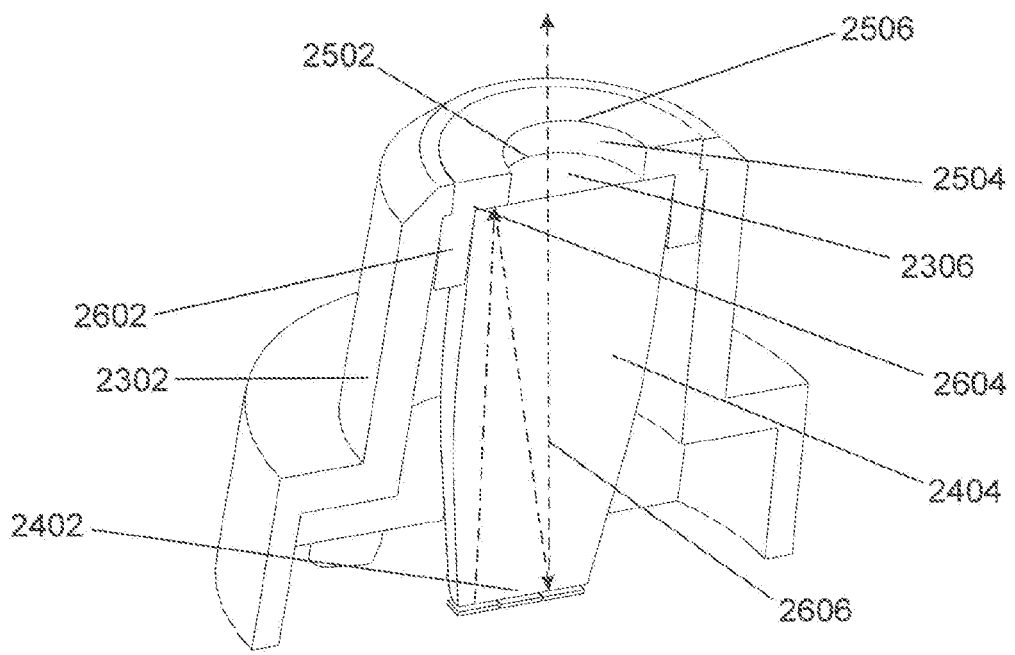
FIG. 26 shows a cross sectional view of the system of FIG. 25.

FIGS. 25 and 26 show a system very similar to FIGS. 23 and 24 for which the only modification is the ratio of the optic diameter to the output aperture diameter of the reflective optic holder with output aperture 2502 indicated in the isometric view of FIG. 25. FIG. 26 shows the system of FIG. 25 in cross sectional view indicating ray path 2606, which starts at the LED die below the input aperture 2402, reflects off the inside face of mirrored holder 2602 back toward the LED array and back out through aperture 2502 and 2506. Again, the inner wall 2504 of holder 2602 is mirrored so that any light hitting it is substantially redirected out of aperture 2506 and is not significantly scattered or absorbed. The system of FIGS. 25 and 26 has an analogous affect as the system of FIG. 21. The material of holder 2602 is preferably a high temperature plastic or could be metal as well. It could be designed with slits along the side walls within the counter bore where the optic goes which could be forced by the shape of holder 2302 to bend in and push against the tapered walls of the optic 2404 and thereby act as a means of holding all three components together. Otherwise a retaining ring could be used to hold the optic and holder 2406 into holder 2302.

Figure 27:
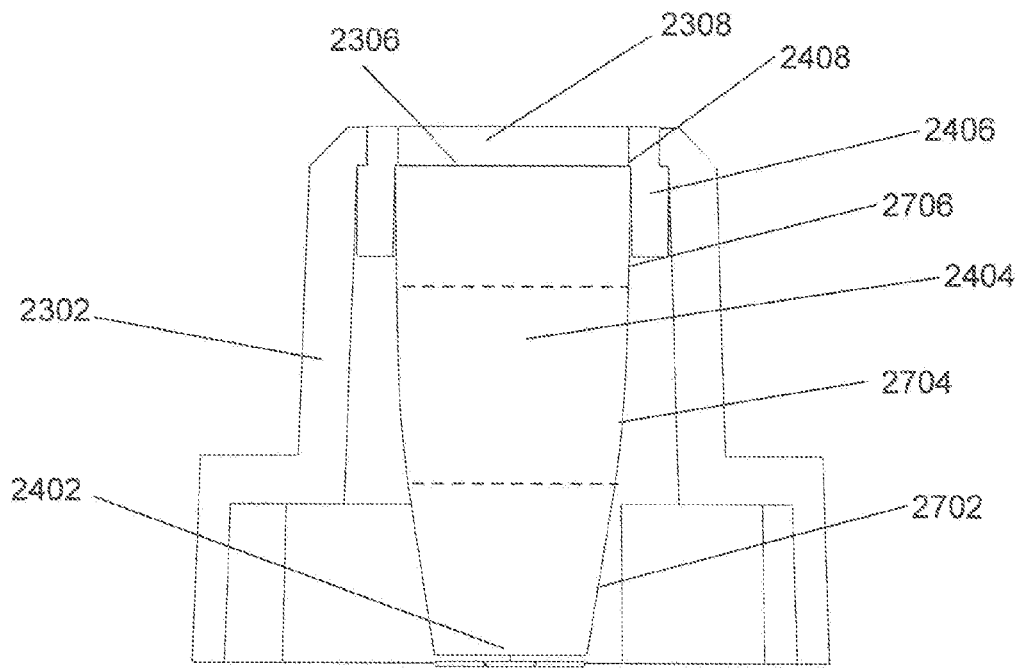
FIG. 27 shows side on cross sectional view of the system of FIG. 23.
Figure 28:
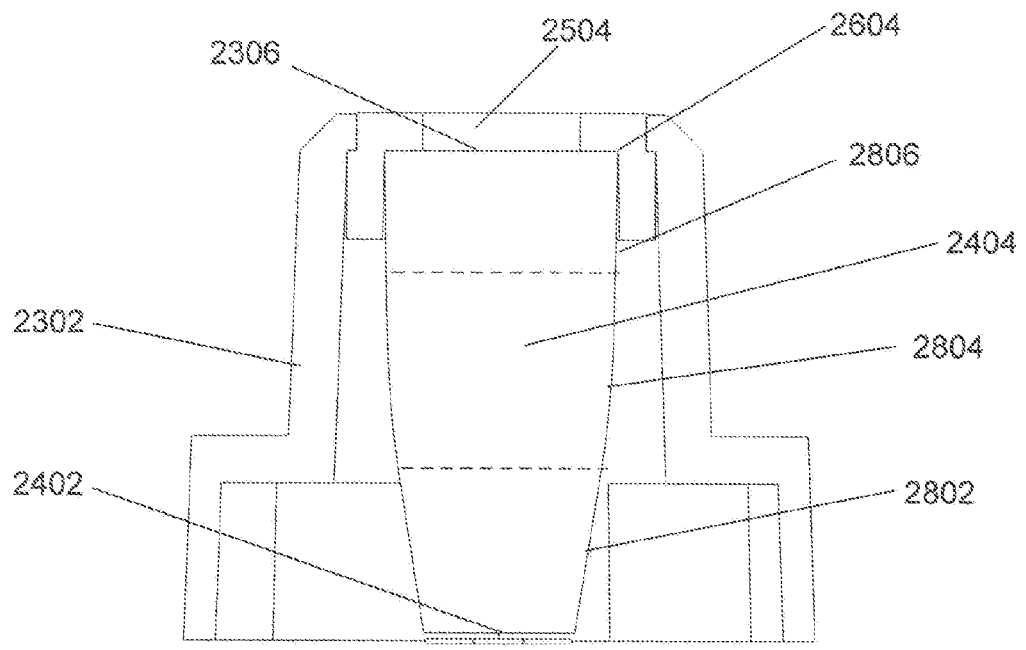
FIG. 28 shows a side on cross sectional view of the system of FIG. 25.

FIGS. 27 and 28 show cross sectional views of the systems of FIGS. 23 and 25, respectively. The optic 2404 of the system of FIG. 27 has sections 2702, 2704 and 2706, which are analogous to sections 2102, 2104, and 2106 of FIG. 22 respectively.

Figure 29:
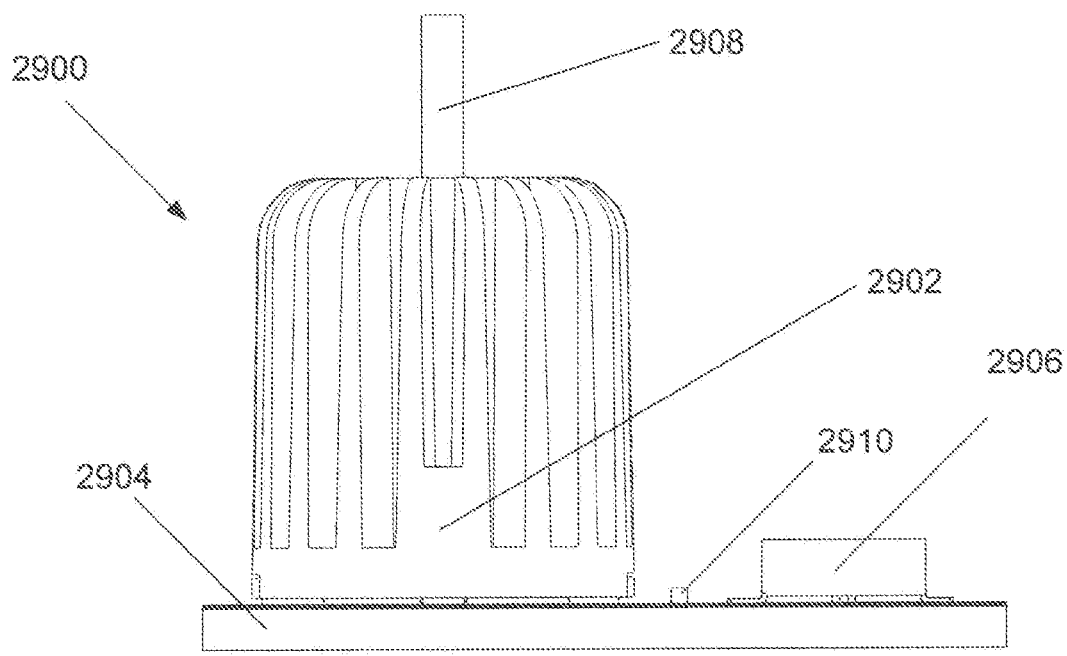
FIG. 29 shows a final embodiment of the system of FIG. 18 which launches high brightness LED light into an optical fiber.
Figure 30:
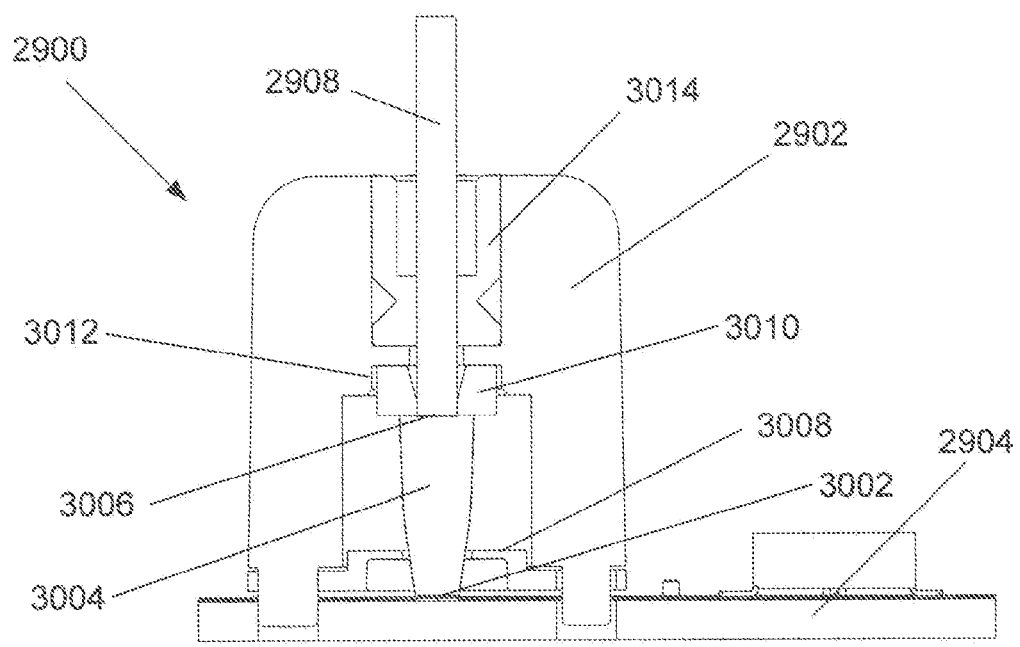
FIG. 30 shows a cross sectional view of the system of FIG. 29.
Figure 31:
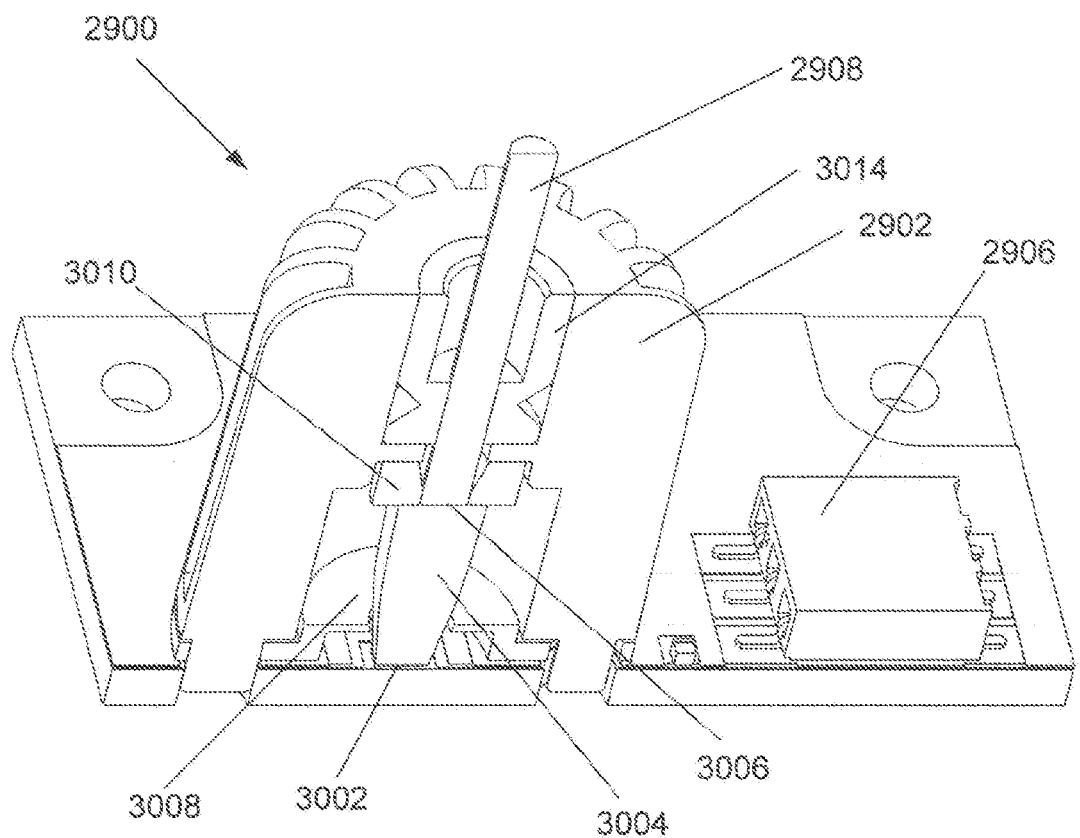
FIG. 31 shows an isometric view of the cross sectional view of the system of FIG. 29.
Figure 32:
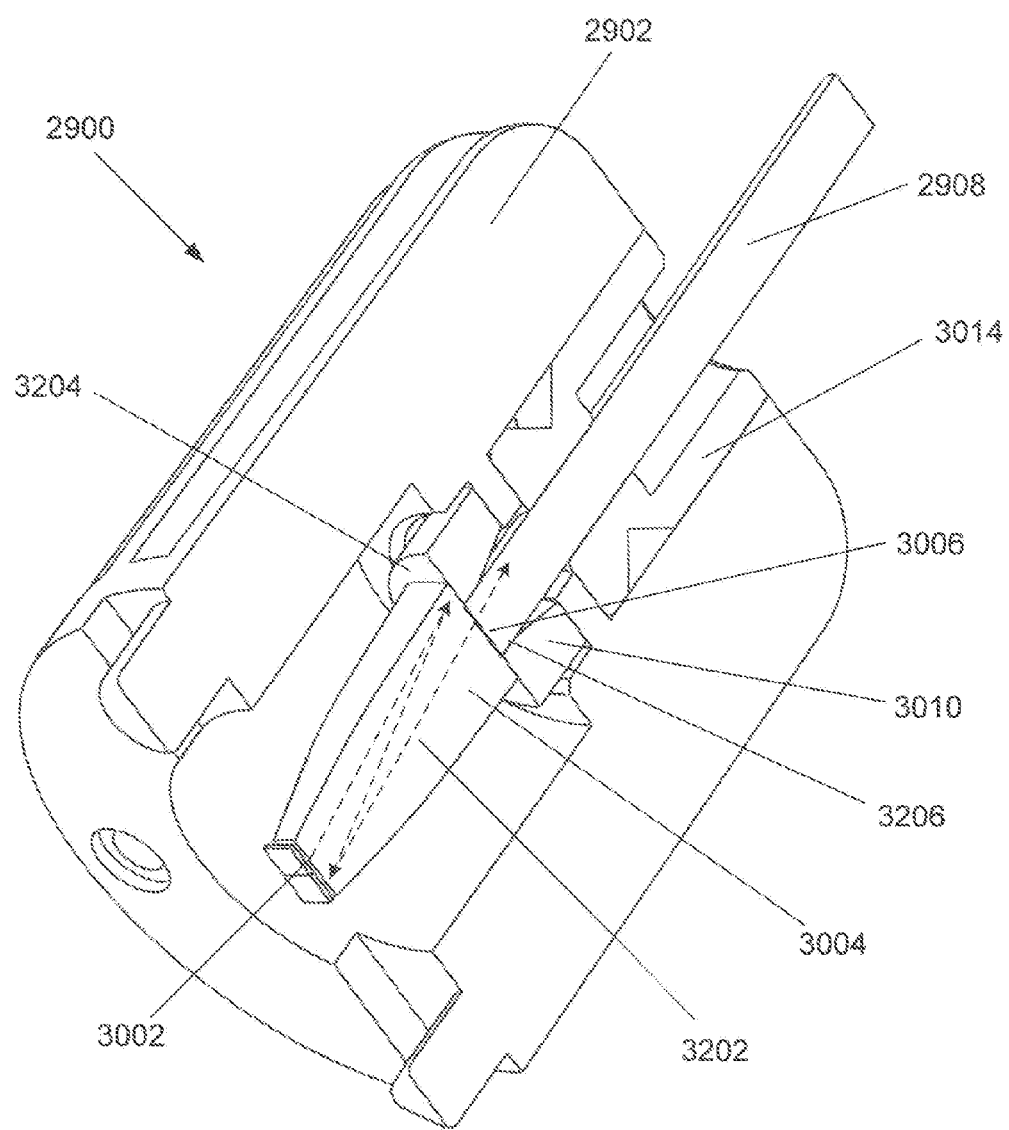
FIG. 32 shows a cross sectional view of the system of FIG. 29 without the LED board showing detial of the mirrored aperture.

FIGS. 29 through 38 show another embodiment 2900 of a LED light engine incorporating a mirrored aperture and designed to interface to an optical fiber or fiber bundle for applications such as endoscopic illumination, which can now replace Xenon arc lamp based systems with much improved lifetime, lower cost, and reduced input power. Furthermore, these systems do not require a high voltage to start them such as is necessary for arc lamps which eliminates EMI (electromagnetic interference) associated with many operating room illumination systems presently in use. FIG. 29 shows LED light engine 2900 with holder 2902 attached to LED board 2904 with light being emitted from attached fiber optic 2908, thermistor temperature sensor 2910 and surface mount connector 2906. FIG. 30 shows a cross sectional view of the system of FIG. 29 showing internal components including the optic 3004, mirrored aperture 3010, fiber 2908, optic retainer 3008, and fiber ferrule 3014. A bevel near the bottom of the fiber holder allows for a set screw through the side of holder 2902 to retain the fiber 2908 in close proximity to the output face of the collection optic 3004 at aperture 3006. Kinematic pins in the holder are shown projecting into holes in the metal core LED board 2904. The bottom side of mirrored aperture 3010 is coated with a high reflectivity coating such as protected aluminum or silver or alternatively, a multilayer reflective dielectric stack coating. Alternatively, a material such as was described above from 3M comprising reflective film could be attached to the bottom of mirror 3010. The fiber 2908 extends out beyond the lower face of the ferrule 3014 so that it can extend through the aperture in 3010. If the inner wall of the hole in the mirror is specularly reflective, then the fiber would not need to be directly against the output aperture 3006 of optic 3004. Again, the LED die, die array or die/phosphor combination would be located on the LED board 2904 centered below the input aperture 3002 of the optic 3004. The function of the mirror of system 3000 is analogous to that of mirror 1802 of FIG. 18. FIG. 31 shows an isometric cross sectional view of the system of FIG. 30 providing a better perspective on the inner components, particularly the optic retainer 3008, which is centered by similar kinematic pins on the bottom of holder 2902. FIG. 32 shows a bottom isometric cross sectional view of the system of FIG. 29 without the board or attached components, with the exception of the LED die at the input aperture 3002 or the optic 3004. Ray path 3202 shows a ray emitted from the LED array reflected off the bottom side of the reflective mirror aperture 3010 at surface 3204, directed by specular reflection back to the LED array or phosphor and then scattered back out the aperture 3006 and into optical fiber 2908.

Figure 33:
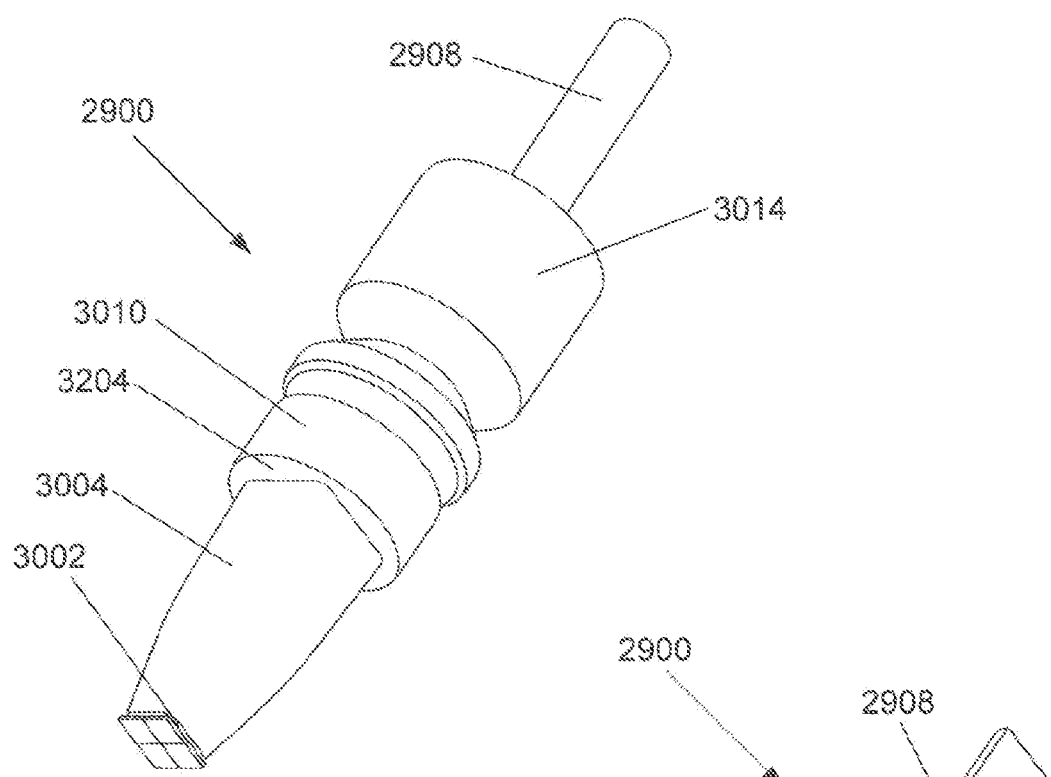
FIG. 33 shows the internal components of the system of FIG. 29.
Figure 34:
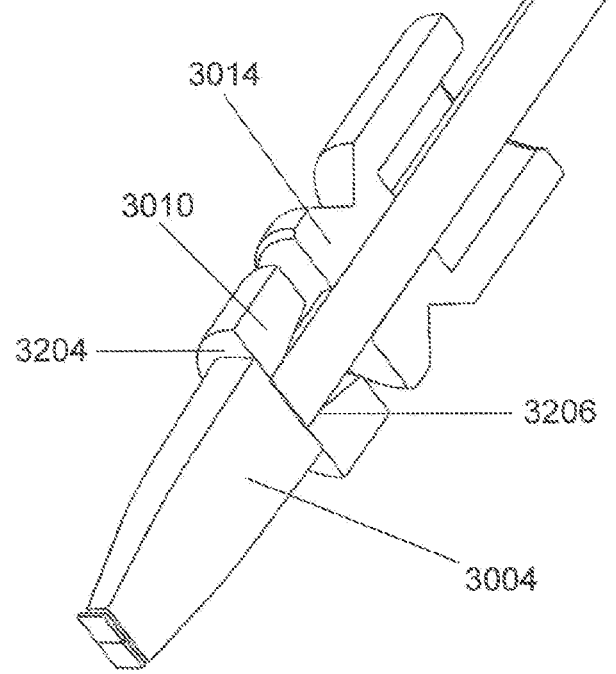
FIG. 34 shows a cross sectional view of the system of FIG. 33.
Figure 35:
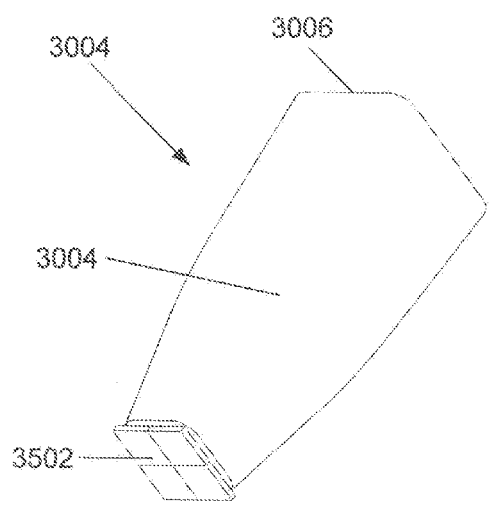
FIGS. 35, 36, 37 and 38 show details of the optic of the system of FIG. 29.
Figure 36:
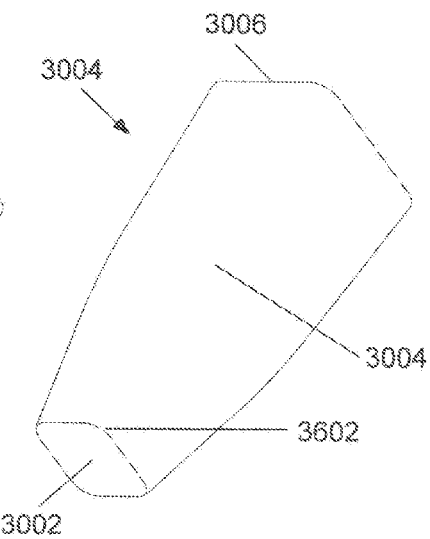
Figure 37:
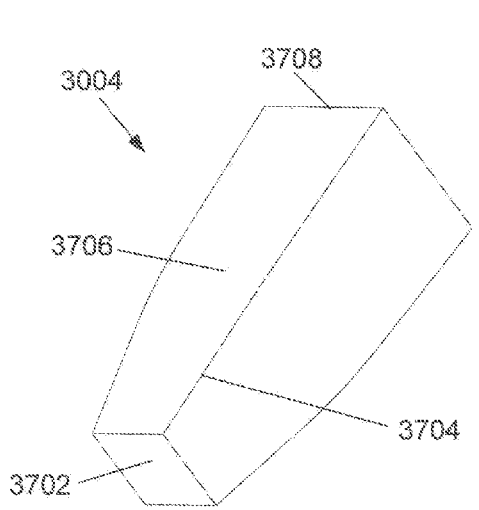
Figure 38:
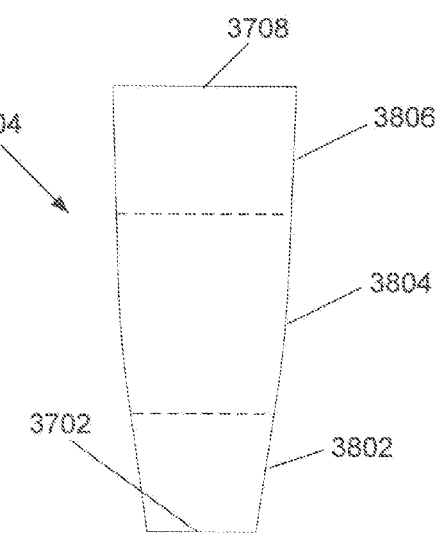

FIG. 33 shows a detail of the system of FIG. 32 with the holder 2902 removed and in cross sectional view in FIG. 34. FIGS. 35 through 38 show detailed views of the optic 3004 of the system of FIG. 33 indicating the square dimensions of input face 3002 relative to square LED array 3502. The output face 3006 is also square in cross section. The corners of the optic have been radiused to make the glass optic easier to release from the mold. There is no loss in performance due to the radiused edge up to a point as the small amount of light lost at the corners of the LED die is made up for by decreasing the ratio of the exit face area to the fiber diameter area, thereby increasing the efficiency of coupling light out through the exit aperture. FIGS. 37 and 38 show the optic 3004 with the edges squared off and without radius in isometric view and cross sectional view, respectively. The sides 3706 are comprised of three sections; 3802 which is conical, 3804 which is parabolic CPC form, and 3806 which is conical in the same manner as the surfaces of optic 1902 of FIG. 22.

Figure 39:
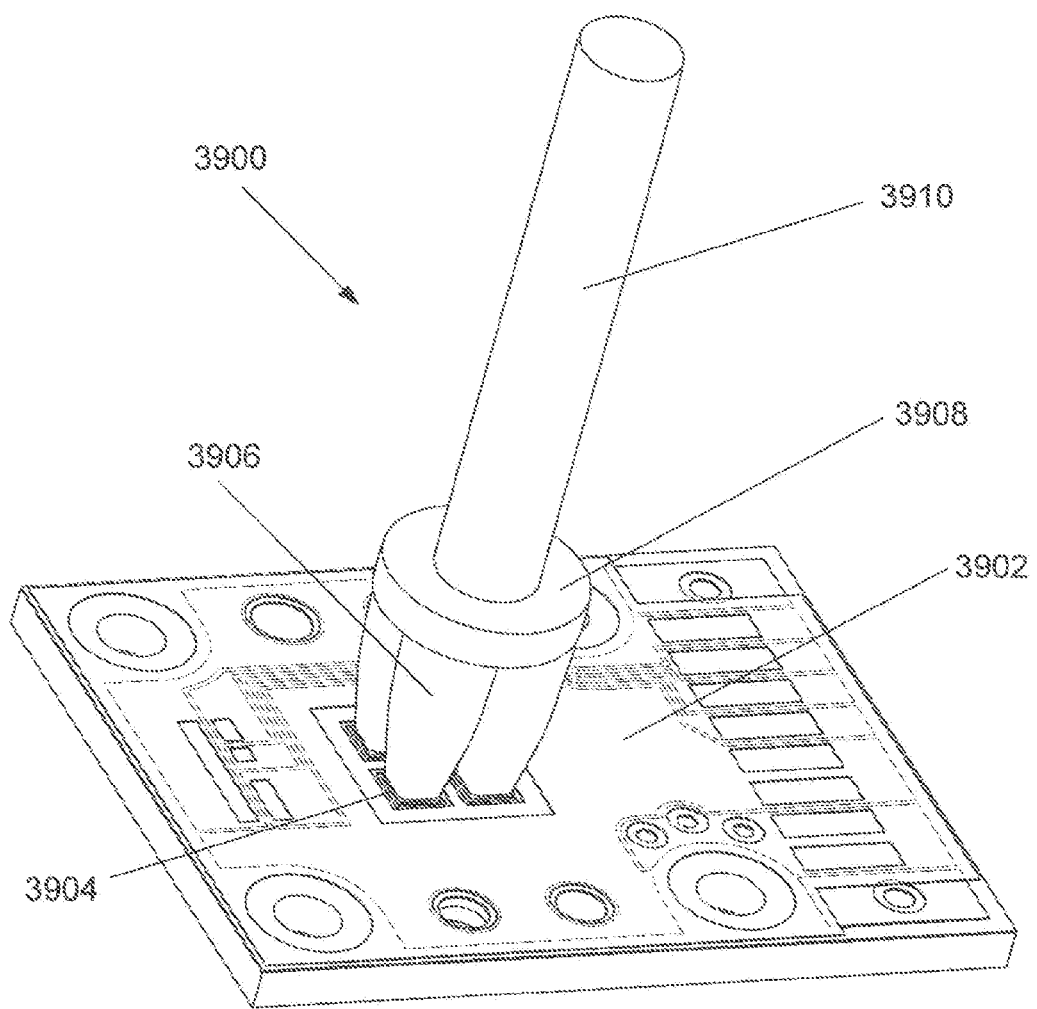
FIG. 39 shows an alternative embodiment using four collection optics in the place of one for the purpose of spreading out the thermal load of the LEDs.
Figure 40:
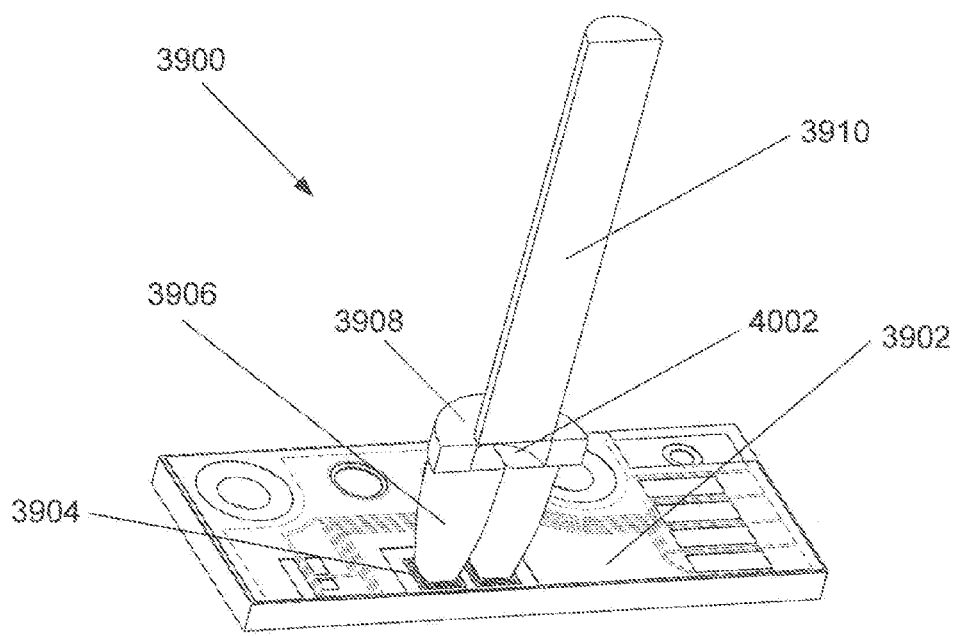
FIG. 40 shows a cross sectional view of the system of FIG. 29.
Figure 41:
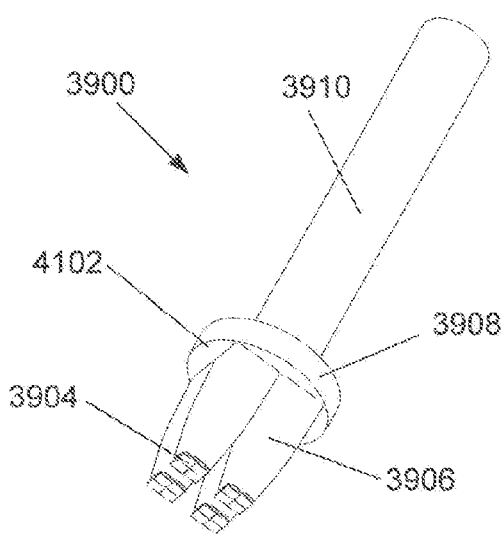
FIG. 41 shows the system of FIG. 39 without the LED board.
Figure 42:
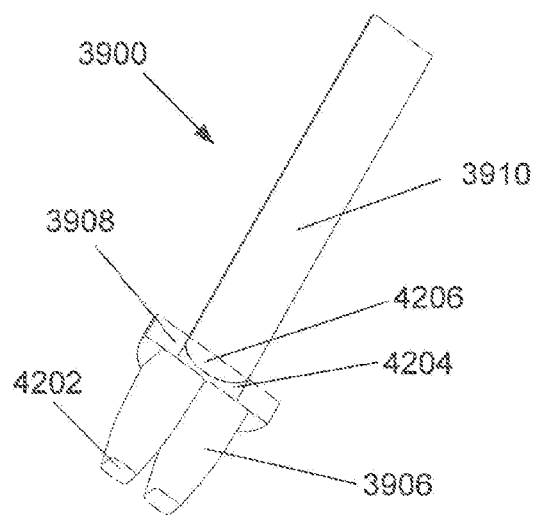
FIG. 42 shows a cross section of the system of FIG. 41 without the LED die showing.

Finally, a system 3900 of FIG. 39 is shown in isometric view representing an alternative embodiment of the system of FIG. 30 for which the single LED array has been replaced with four (4) separate LED arrays 3904 at the input apertures of four individual collection optics 3906. The apertured mirror 3908 is positioned at the output faces of the collection optics 3906 and centered on the central axis of the four arrays attached to LED board 3902. The optical fiber or fiber bundle 3910 interfaces to the output of apertured mirror 3908. FIG. 40 shows a cross sectional isometric view of the system of FIG. 39 indicating an overlap between the output apertures 4002 of the optics 3906 and the central aperture of mirrored reflector 3908. FIGS. 41 and 42 show an isometric bottom view of the system of FIG. 39 without the LED board indicating the separation between the four groups of LED die and in cross sectional view, respectively. The lower side 4102 of apertured mirror 3908 is highly reflective as would be the inside of the aperture at cylindrical surface 4204. Thus, the fiber 3910 is butt-coupled to and centered on apertured mirror 3908. The benefit of the system of FIG. 39 over using a single optic is thermal in nature. By virtue of increasing the distance between the heat sources (LED die) on the LED board, the heat flux is reduced, and the die can be maintained at a lower temperature for a given degree of cooling. If this improved output due to the improved thermal performance outweighs the disadvantage of a more complex system then there is a net benefit to this configuration. It is clear from the separation of the LED die groups in FIG. 41 that the thermal situation would be improved. In particular for the inner most LED die, which in a 4 by 4 array of 16 die would be completely surrounded by other LED heat loads.

For all the systems indicated above it is well known in the art that the transmission efficiency could be further enhanced by the addition of anti-reflection coatings on any air-dielectric interfaces. Additionally, the optical shapes shown could be approximated by faceted optics with some loss in Etendue maintenance. Additionally, other types of emitters including organic light emitting diodes and laser diodes could be substituted for the LEDs. Other variations will occur to those skilled in the art and are intended to be within the scope of the appended claims.

What is claimed is:

1. A lighting apparatus for producing high brightness, said lighting apparatus comprising:
    a high thermal conductivity printed circuit board;
    at least one bare LED die comprising one or more LED emitting areas for generating radiation of one or more spectral bands over a predetermined solid angle, said at least one bare LED die being attached to said high thermal conductivity printed circuit board with a thermally conductive bonding layer;
    an electronic control module attached to said high thermal conductivity printed circuit board for controlling the output of said LED emitting areas;
    a photosensor attached to said high thermal conductivity printed circuit board at a predetermined spaced apart location with respect to said LED die for providing a feedback signal to said electronic control module to regulate the output of said LED emitting areas; and
    at least one non-imaging concentrator fixedly attached to and in registration with said high thermal conductivity printed circuit board, said non-imaging concentrator having entrance and exit apertures, said non-imaging concentrator entrance aperture being optically aligned with said LED emitting areas for collecting radiation from said LED emitting areas and re-emitting it through said non-imaging concentrator exit aperture with an étendue substantially the same as that of said LED emitting areas, said non-imaging concentrator having prismatic optical elements positioned near said exit aperture for sampling the light emitted near said exit aperture and directing it along a folded optical path to said photosensor as an optical signal indicative of the intensity of radiation exiting said non-imaging concentrator.

2. The lighting apparatus of claim 1 wherein said nonimaging concentrator re-emits substantially all of the radiation collected thereby as a diverging beam having a solid angle smaller than said predetermined solid angle over which radiation is emitted by each of said LED emitting areas.

3. The lighting apparatus of claim 1 further including a shroud for preventing stray radiation that may emerge from said non-imaging concentrator from entering said folded optical path between the point near said non-imaging concentrator exit aperture from which the intensity of radiation is sampled and said photosensor and directly from said LED emitting areas to said photosensor.

4. The lighting apparatus of claim 1 further including a heat sink thermally bonded to said high thermal conductivity printed circuit board on the side opposite to that on which other components are attached to selectively dissipate heat generated in the process of converting electrical energy to optical power to enhance the quantum efficiency of said lighting apparatus.

5. The lighting apparatus of claim 1 further including a thermistor mounted on said high thermal conductivity printed circuit board to monitor temperature and provide a feedback signal to said electronic control to assist in regulating the operating temperature of said apparatus and the output of said LED emitting areas.

6. The lighting apparatus of claim 1 further including an electronic plug attached to said high thermal conductivity printed circuit board along with wires running from said electronic plug and bonded to the various other components attached to said high thermal conductivity printed circuit board to provide electrical communication between the components mounted on said high thermal conductivity printed circuit board and a power source.

7. The lighting apparatus of claim 1 wherein said at least one bare LED die comprises an array of regularly spaced LED die and an array of spaced apart non-imaging concentrators the individual non-imaging concentrators of which are optically coupled in one-to-one correspondence with said regularly spaced LED die.

8. The lighting apparatus of claim 1 wherein said spectal bands of said LED emitting areas range from the ultra violet to near to mid infrared.

9. The lighting apparatus of claim 1 wherein said non-imaging concentrators have cross-sectional shapes selected from the group consisting of compound parabolic, compound elliptical, compound hyperbolic concentrators, straight tapers, and concentrators having curvatures described by higher order polynomial functions or combinations thereof.

10. The lighting apparatus of claim 9 wherein said non-imaging concentrators further include a homogenizing section located forward of said entrance aperture to promote uniform color and intensity distribution in said apparatus output.

11. The lighting apparatus of claim 5 wherein said non-imaging concentrators are rectangular in cross section to control the divergence of said diverging beam in vertical and horizontal planes mutually perpendicular to said optical axis.

12. The lighting apparatus of claim 1 wherein said non-imaging concentrator is fabricated of a material selected from the group consisting of optical plastic, molded glass, and silicone.

13. The lighting apparatus of claim 1 further including a mirror surface surrounding the perimeter of said exit aperture and facing said high thermal conductivity printed circuit board to intercept radiation that does not directly pass through said exit aperture from said LED emitting areas and direct it back toward said LED emitting areas to be reflected therefrom through said exit aperture to increase the light coupled out of said exit aperture over that which would be achieved without the use of said mirror surface.

14. The lighting apparatus of claim 1 wherein said non-imaging concentrator comprises a first conical section having an input side that is non-index matched to said LED emitting areas, followed by a second section that is parabolic in cross section, together comprising a $\theta_{in}$ by $\theta_{out}$ compound parabolic concentrator and connecting with the output side of said first conical section such that at their interface they share a common tangent, and a third conical section coupled to said second parabolic section.

15. The lighting apparatus of claim 1 wherein said non-imaging concentrator comprises an integrating section that has a cross sectional shape that transitions between a square and a circle, a second conical section, followed by a third section that is parabolic in cross section, second and third sections together comprising a $\theta_{in}$ by $\theta_{out}$ compound parabolic concentrator and connecting with the output side of said second conical section such that at their interface they share a common tangent, and a fourth conical section coupled to said third parabolic section.

16. The lighting apparatus of claim 1 wherein said non-imaging concentrator comprises a square homogenizing section followed by a lofted section that has a square input coupled to said square homogenizing section which then transitions to a round exit aperture.

17. The lighting apparatus of claim 1 wherein said non-imaging concentrator has a cross-sectional shape that transitions between a rectangular input aperture and a circular output aperture.

18. The lighting apparatus of claim 1 wherein said non-imaging concentrator has a cross-sectional shape that is rectangular.

19. The lighting apparatus of claim 1 wherein said non-imaging concentrator comprises a housing section and an optic section that are integrally molded, said housing section having locating pins that fit into complementary configured holes in said high thermal conductivity printed circuit board to locate said non-imaging concentrator with respect to said high thermal conductivity printed circuit board.

20. The lighting apparatus of claim 19 wherein said housing section and said optic section are separate pieces and further includes an intermediate section for holding said optic section near its output end to position it with respect to said housing section.

21. The lighting apparatus of claim 20 wherein said housing section is a ferrule for positioning and holding an optical fiber with respect to the output of said non-imaging concentrator.

22. A lighting apparatus for use with optical fibers, said lighting apparatus comprising:
    a high thermal conductivity printed circuit board;
    at least one bare LED die comprising one or more LED emitting areas for generating radiation of one or more spectral bands over a predetermined solid angle, said at least one bare LED die being attached to said high thermal conductivity printed circuit board with a thermally conductive bonding layer;
    an electronic control module attached to said high thermal conductivity printed circuit board for controlling the output of said LED emitting areas;
    at least one non-imaging concentrator fixedly attached to and in registration with said high thermal conductivity printed circuit board, said non-imaging concentrator having entrance and exit apertures, said non-imaging concentrator entrance aperture being optically aligned with said LED emitting areas for collecting radiation from said LED emitting areas and re-emitting it through said non-imaging concentrator exit aperture with a predetermined étendue, and
    a holder mounted to said high thermal conductivity printed circuit board, said holder having a first bore for receiving a ferrule for positioning an optical fiber with respect to said exit aperture of said non-imaging concentrator and a second bore for receiving a retainer for positioning the exit aperture of said non-imaging concentrator with respect to said housing, said retainer having a mirrored surface facing said LED emitting areas for directing light therefrom not directly exiting said exit aperture back to said LED emitting areas for reflection back through said exit aperture to enhance the output from said non-imaging concentrator.

* * * * *